United States Patent
Yamashita et al.

(10) Patent No.: US 6,950,767 B2
(45) Date of Patent: Sep. 27, 2005

(54) QUALITY MONITORING SYSTEM FOR BUILDING STRUCTURE, QUALITY MONITORING METHOD FOR BUILDING STRUCTURE AND SEMICONDUCTOR INTEGRATED CIRCUIT DEVICE

(75) Inventors: Shunzo Yamashita, Tokyo (JP); Kei Suzuki, Kokubunji (JP); Toshiyuki Aritsuka, Kodaira (JP); Sadaki Nakano, Kokubunji (JP)

(73) Assignee: Renesas Technology Corp., Tokyo (JP)

( * ) Notice: Subject to any disclaimer, the term of this patent is extended or adjusted under 35 U.S.C. 154(b) by 0 days.

(21) Appl. No.: 10/706,972

(22) Filed: Nov. 14, 2003

(65) Prior Publication Data

US 2004/0153270 A1 Aug. 5, 2004

(30) Foreign Application Priority Data

Nov. 15, 2002  (JP) ...................................... 2002-331532

(51) Int. Cl.⁷ .............................................. G06F 19/00
(52) U.S. Cl. .......................... 702/81; 702/104; 340/665; 340/686.1; 340/572.1
(58) Field of Search .............................. 702/81, 47, 52, 702/53, 104; 340/10.41, 665, 686.1; 360/60, 69, 75

(56) References Cited

U.S. PATENT DOCUMENTS 6,617,963 B1 * 9/2003 Watters et al. ........... 340/10.41

FOREIGN PATENT DOCUMENTS

| EP | 0 491 567 A1 | 6/1992 |
| EP | 1 162 767 A2 | 12/2001 |
| JP | 5-82890 | 11/1993 |
| JP | 7-50104 | 2/1995 |
| JP | 8-082535 | 3/1996 |
| JP | 9-304127 | 11/1997 |
| JP | 2000-32732 | 1/2000 |
| JP | 2001-201373 | 7/2001 |
| JP | 2002-39810 | 2/2002 |
| JP | 2002-135348 | 5/2002 |
| WO | WO 00/05849 | 8/2000 |

* cited by examiner

Primary Examiner—Bryan Bui
Assistant Examiner—Hien Vo
(74) Attorney, Agent, or Firm—Antonelli, Terry, Stout and Kraus, LLP.

(57) ABSTRACT

A low cost system and method are provided for long-term monitoring of the quality of a building structure utilizing a semiconductor integrated circuit device buried in the structure. A monitoring chip includes a sensor, a microprocessor, a memory, a radio interface, an electric power controller and an electric power generator. The monitoring chip intermittently receives power to intermittently monitor information such as whether concrete is adequately cured, whether the quantity of moisture and chloride ions in concrete paste is adequate, or whether a state of stress inside concrete is in question. Temperature sensors, electric resistance sensors and pressure sensors respectively built in the monitoring chip use the built-in electric power generator as a power source, and the system store any abnormal measured values in a built-in memory. Collected quality data is transmitted according to an external request to indicate building structure quality.

29 Claims, 20 Drawing Sheets

| CHIP-ID | DISTANCE | DIRECTION |
|---|---|---|
| #1 | 0.5m | +90, -30° |
| #2 | 0.7m | +15, -15° |
| #3 | 0.1m | -50, +32° |
| #4 | 0.2m | -30, +75° |
| ⋮ | ⋮ | ⋮ |

PD400

| CHIP-ID | SENSOR ID | DETECTED DATA |
|---|---|---|
| #1 | #1 | $1.0 \times 10^{-9}$ |
| #1 | #3 | $2.1 \times 10^{1}$ |
| #2 | #2 | $3.5 \times 10^{1}$ |
| #3 | #1 | $3.5 \times 10^{1}$ |
| ⋮ | ⋮ | ⋮ |

SD400

QUALITY MONITORING SYSTEM FOR BUILDING STRUCTURE, QUALITY MONITORING METHOD FOR BUILDING STRUCTURE AND SEMICONDUCTOR INTEGRATED CIRCUIT DEVICE

FIELD OF THE INVENTION

The present invention relates to a quality monitoring method for building structure constructible at a low cost, a monitoring system and a semiconductor integrated circuit device for the monitoring system required for realizing them.

BACKGROUND OF THE INVENTION

Recently, in building structure formed by concrete such as a tunnel, an accident in which concrete flakes comes into question and the enhancement of the quality of concrete building structure is severely demanded. To realize it, technique for promptly realizing the quality checking of building structure at a low cost is essential. Therefore, many methods of semiautomatically inspecting the quality of building structure nondestructively by an external inspection device are proposed.

In the meantime, a method of building various sensors in building structure beforehand when the building structure is constructed, constantly measuring/monitoring physical quantity such as stress by the sensors and monitoring the quality of the building structure or monitoring systems are also proposed. As in these monitoring systems, quality judgment is theoretically substantially automated, labor for quality judgment can be reduced.

Of these, for example, in a nonpatent document 1, an idea that an optical fiber sensor which can sense strain applied to itself is installed in building structure and stress applied to steel structure supporting the building structure is constantly monitored to utilize for the assurance of the earthquake-proof performance of the building structure is disclosed.

In the meantime, in a patent document 1, an idea that a strain gauge is laid on a reinforcing bar, the electric resistance of the strain gauge is measured and the quality of building structure is monitored at real time is disclosed. According to this document, stress in the building structure can be measured by the strain gauge and the result of monitoring can be utilized for maintenance and others. Though the concrete configuration is not described, an idea that a pH sensor is utilized for judging a degree of the deterioration of building structure is also disclosed.

Further, in a nonpatent document 2, a system that a sensor and a wireless installation are integrated and data detected by radio can be transmitted to external measurement equipment and others and can be monitored is disclosed. Concretely, an example that in a monitoring system in which a small-sized radio module the power consumption of which is little and a sensor that can detect vibration such as an acceleration sensor are integrated, a response to an earthquake wave in building structure such as an office building, that is, the earthquake-proof performance is measured is introduced.

Further, in a nonpatent document 3, it is disclosed that a floor, a wall and a human body constantly vibrate though the vibration is minute and they normally have the energy density of $-mW/cm^3$.

Besides, in a nonpatent document 4, the configuration of an electric power generator that converts minute vibrational energy disclosed in the nonpatent document 3 to electric energy is disclosed.

In a patent document 2, the configuration of a pressure sensor (a strain gauge resistance type) that can be produced in a semiconductor process is disclosed.

Further, in a patent document 3, the configuration of a pressure sensor (an electrostatic capacity type) that can be similarly produced in a semiconductor process is disclosed.

Further, in a nonpatent document 5, ultra wide band (UWB) technique which is an ultra wide band telecommunication system is disclosed. As disclosed in this document; UWB technique enables telecommunication at ultralow power consumption. This document discloses that high-precision positional detection and the measurement of distance can be realized.

Further, in a nonpatent document 6, various factors that determine the strength of concrete are disclosed. Particularly, in this document, it is disclosed that a management period (hereinafter called curing) in which hydration proceeds after concrete casting and the strength of the concrete is manifest has a great effect upon the strength of the concrete. Concretely, information that heat caused in hydration has a bad effect upon the manifestation of strength is disclosed.

Besides, in a nonpatent document 7, it is described that a degree of the proceedings of the corrosion of a reinforcing bar in concrete can be estimated based upon a value of the electric resistance of concrete.

Further, in a nonpatent document 8, the details of the transmission characteristic of an electromagnetic wave in concrete are described.

[Patent Document 1]
  Japanese published unexamined patent application No. 2002-38723
[Patent Document 2]
  Japanese published unexamined patent application No. Hei11-121766
[Patent Document 3]
  Japanese published unexamined patent application No. 2001-99734
[Nonpatent Document 1]
  http://www.mita.sd.keio.ac.jp/papers/index.htm(d own load date:2002.08.01; Proc. Second International Workshop on Structural Health Monitoring, 1999, pp. 56 to 67 corresponds to the content of the URL)
[Nonpatent Document 2]
  Nikkei Electronics, Jul. 17, 2002, pp. 37
[Nonpatent Document 3]
  IEEE Computer July 2000, pp. 42 to 48
[Nonpatent Document 4]
  IEEE TRANSACTIONS ON VERY LARGE SCALE INTEGRATION SYSTEMS, VOL. 9, NO. 1, FEBRUARY 2001, pp. 64 to 75
[Nonpatent Document 5]
  Nikkei Electronics Mar. 11, 2002, pp. 55 to 66
[Nonpatent Document 6]
  "Illustrated concrete" published by Ohm, pp. 95 to 111
[Nonpatent Document 7]
  99' annual report published by Power Central Research Institute, pp. 92 to 93
[Nonpatent Document 8]
  http://www.tuat.ac.jp/~masa/study-j.html

SUMMARY OF THE INVENTION

As disclosed in the nonpatent document 6, the quality of concrete which is the basis of a modern building is mainly determined by 1) the mixture ratio of cement and water when concrete paste is prepared (whether more moisture than quantity required is included or not), 2) the quality of the aggregate of concrete paste (whether gravel including much salinity is used or not), 3) impurities in concrete paste (whether refuse and others are mixed or not) and 4) the quality of work (whether concrete is accurately managed and cured or not). In the above-mentioned accident in the tunnel in which concrete flakes, it is considered that the use of concrete paste including salty sea sand in large quantities in which water is mixed in large quantities in addition to enhance efficiency when concrete is cast and to facilitate handling is the largest cause. That is, it is considered that as inadequate concrete paste is used, a chloride ion included in sea sand corrodes the steel structure of foundation, further, a part from which moisture in the concrete paste is evaporated becomes void, as a result, the concrete becomes very fragile and starts to flake in time greatly shorter than a designed life.

As described above, it is no exaggeration to say that the quality of concrete building structure is substantially determined in the preparation, the casting and the curing of concrete. Therefore, quality control/a quality test in the preparation, the casting and the curing of concrete is very important. Regretfully, in a current state in which cases that inadequate concrete is used continue, the quality checking of concrete itself is also very important.

In the meantime, the quality monitoring system for building structure and the monitoring method disclosed in the patent document 1 and the nonpatent documents 1 and 2 are basically the monitoring system for building structure already constructed or the monitoring method and they cannot be effective means to solve the problems. Particularly, it is impossible to detect whether inadequate concrete is cast or not immediately on the spot. Similarly, in the monitoring system or the monitoring method, stress and vibration can be measured, however, above 1) to 4) cannot be directly measured. Therefore, there is a problem that even if inadequate concrete is used in construction, inside steel structure and others are extremely deteriorated after ten years or more elapse since the construction and after flaking and collapse start or immediately before they start, it is known that inadequate concrete material is used.

In the patent document 1, an idea that the quality of building structure is determined using a pH sensor is also described. The concrete configuration is not described in this document, however, if the pH sensor is used, the quality of the aggregate of concrete paste described in the above-mentioned problem 2) can be basically measured. However, in the case of the monitoring system in this document, it cannot be measured until building structure is completed and sensors built in the building structure are connected to measurement equipment. That is, there is a problem that the monitoring system and the monitoring method disclosed in this document cannot be used for quality control and quality checking in concrete paste preparation, concrete casting and curing.

Further, there is a problem that as a sensor such as a very high-priced optical fiber sensor is required in the monitoring system and the monitoring method, the cost is high. Besides, there is a problem that as a sensor built in building structure is required to be connected to a cable (an optical fiber or a metal fiber), the construction cost is high. Further, there is a problem that for a basic problem, in case a coupling cable is disconnected because of any careless cause, the monitoring system is disabled.

The object of the invention is to monitor the quality of concrete since concrete paste is prepared which has the greatest effect upon the quality, the life and a degree of the deterioration of building structure, in other words, whether inadequate concrete is used or not and to provide a method of overall monitoring the quality of the building structure and others and a monitoring system.

Further, another object of the invention is to provide a semiconductor integrated circuit device in which an electric power generator, a sensor, CPU, a memory and a radio interface are built to realize the above-mentioned monitoring system and which can permanently monitor the quality of concrete since concrete paste is prepared.

Further, another object of the invention is to provide a quality monitoring system for building structure and a quality monitoring method for building structure which enable quality control and quality checking in concrete paste preparation, concrete casting and curing and a semiconductor integrated circuit device used for them.

Further, another object of the invention is to provide a quality monitoring system for building structure and a quality monitoring method for building structure which can realize quality control and quality checking in concrete paste preparation, concrete casting and curing at a low price without using a high-priced sensor such as an optical fiber sensor and a semiconductor integrated circuit device used for them.

Further, another object of the invention is to provide a quality monitoring system for building structure and a quality monitoring method for building structure in which a sensor is built in the building structure and is not required to be connected to a cable such as an optical fiber cable and a metal cable and which is free from insufficiency by the disconnection of a cable and a semiconductor integrated circuit device used for them.

To briefly explain the outline of the representative of the invention, it is as follows. That is, a semiconductor integrated circuit device (SC1) provided with a first semiconductor integrated circuit (CHIP1) where a sensor that detects physical quantity to be measured, typically an electric resistance sensor (RS1), a temperature sensor (TS1), a pressure sensor (PS1) and an acceleration sensor (AS1), an/a analog/digital (A/D) conversion circuit (AD1) that amplifies a signal detected by the sensor and converts it to a digital signal, a microprocessor (CCPU1) that processes the digital signal, a memory (CMEM1) that stores information acquired by the sensor, a radio interface (CANT1) and an antenna (CANT1) that transmit the signal processed by the microprocessor to an external device by radio, a rectifier (REF1) connected to the antenna, an electric power controller (PC1) that determines whether electric power is supplied to the sensor, the A/D converter, the microprocessor, the memory and the transmitter circuit or not, an electrical charge monitor (CW1) that determines whether the electric power controller is turned on or not and a timer circuit (TM1) are mounted, a capacitor (C1) mounted on a first substrate (BO1) on which the first semiconductor integrated circuit is mounted and a first semiconductor integrated circuit for generating electric power (BCHIP1) is buried in a wall or a floor made of concrete (CON1) for forming building structure (BUL1) at the stage of concrete paste. When minute electric power generated by the built-in electric power generator BCHIP1 is stored in the capacitor C1 by the semiconductor integrated circuit device SC1 buried as described above and electrical charge of preset quantity is stored, the built-in sensors (RS1, TS1, PS1, AS1), the memory CMEM1, the processor CCPU1 and the A/D converter AD1 are intermittently activated and physical quantity such as electric resistance, temperature and pressure in concrete is detected. Further, it is judged by the processor CCPU1 whether a value of a detect signal is within a desirable range or not and in case the value is in an undesirable range, it is stored in the memory CMEM1. The above-mentioned detecting operation is continued at a preset suitable time interval and the quality of concrete is monitored. A detect signal measured as described above is read by an inspection device (RC1) by radio communication after the curing of concrete is finished. Prior to the reading operation, electric power is supplied to the semiconductor integrated circuit device SC1 at a high frequency via the antenna ANT1 of the inspection device RC1 from the ratio interface RF1 in the inspection device RC1. After in the semiconductor integrated circuit device SC1, supplied high-frequency electric power is converted to D.C. electric power by the built-in rectifier REF1, it is stored in the capacitor C1 as a power source for activating the radio interface CRF1 mounted in SC1. As described above, the quality monitoring system for building structure characterized in that data stored in the memory CMEM1 is transmitted to the inspection device and the quality of the building structure is determined by a quality determination program QPR1 in the inspection device is acquired.

The quality monitoring method for building structure according to the invention is characterized in that the method includes a step for building the semiconductor integrated circuit device SC1 in the building structure, a step for operating the sensors (RS1, TS1, PS1, AS1) built in the semiconductor integrated circuit device SC1 for detection, a step for transmitting the result of detection to the inspection device RC1 via the antenna CANT1 through the radio interface CRF1 and a step for determining the quality of the building structure based upon a signal transmitted to the inspection device by the inspection device. The quality monitoring method for building structure may also include a step for storing a detect signal in the memory CMEM1 provided to the semiconductor integrated circuit device SC1 and a step for extracting a signal stored in the memory CMEM1 provided to the semiconductor integrated circuit device SC1 in addition.

Besides, the semiconductor integrated circuit device (SC1) according to the invention is characterized in that it is provided with the first semiconductor integrated circuit (CHIP1) mounting the electric resistance sensor (RS1), the temperature sensor (TS1), the pressure sensor (PS1), the acceleration sensor (AS1), the A/D converter (AD1) that amplifies a signal detected by the sensor and converts it to a digital signal, the microprocessor (CCPU1) that processes the digital signal, the memory (CMEM1) that stores information acquired by the sensor, the radio interface (CANT1) and the antenna (CANT1) that transmit the signal processed by the microprocessor to an external device by radio, the rectifier (REF1) connected to the antenna, the electric power controller (PC1) that determines whether electric power is supplied to the sensor, the A/D converter, the microprocessor, the memory and the transmitter circuit or not, the electrical charge monitor (CW1) that determines whether the electric power controller is turned on or not and the timer (TM1), the capacitor (C1) mounting on the first substrate (BO1) mounting the first semiconductor integrated circuit and the first semiconductor integrated circuit for generating electric power (BCHIP1).

BRIEF DESCRIPTION OF THE DRAWINGS

FIG. 14 show a high-frequency transmitter/receiver of the quality inspection device shown in FIG. 12 and the principle of a method of detecting the position of the monitoring chip realized by it;

DETAILED DESCRIPTION OF THE PREFERRED EMBODIMENTS

Figure 1:
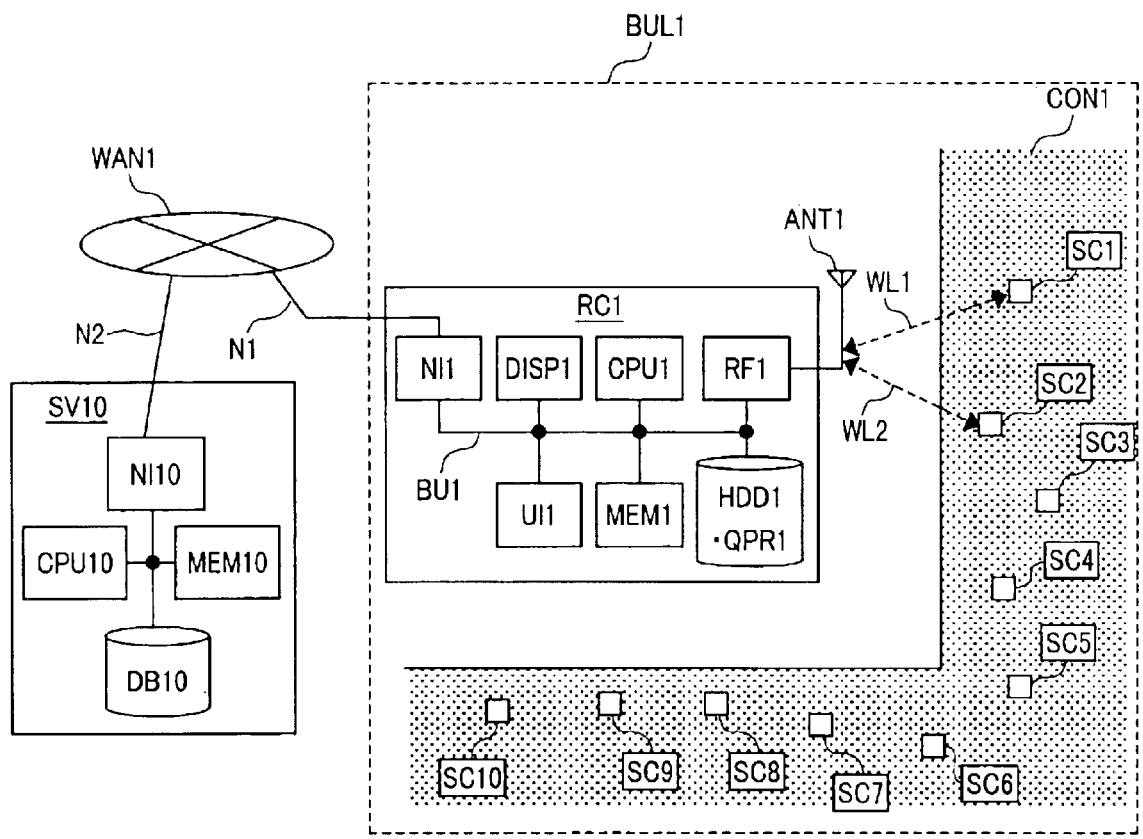
FIG. 1 shows desirable one embodiment of a quality monitoring system for building structure according to the invention.

Referring to the drawings, embodiments of the invention will be described in detail below. In the drawings, the same reference number shows the same or similar part.

First Embodiment

FIG. 1 shows one embodiment of a quality monitoring system for building structure according to the invention. As shown in FIG. 1, the quality monitoring system for building structure according to the invention is composed of an inspection device (RC1) specific to the invention and semiconductor integrated circuit devices specific to the invention, that is, monitoring chips (SC1 to SC10) buried in concrete (CON1) forming a wall and a floor of building structure (BUL1) when concrete paste is prepared as described later. If necessary, a management server (SV10) installed inside the building structure BUL1 or outside BUL1 may be also used. In FIG. 1, an example that ten monitoring chips are used is shown, however, it is an example for explanation and actual use is not limited to the example.

The inspection device (RC1) specific to the invention is composed of an antenna (ANT1), a radiocommunication interface (RF1), a processor (CPU1), a memory (MEM1), a secondary storage (HDD1), a display (DISP1), a user interface (UI1) and a network interface (NI1). Of these, the secondary storage HDD1 is typically formed by a hard disk. The display DISP1 is CRT and others and the user interface UI1 is formed by a keyboard or a mouse.

The inspection device RC1 communicates with the monitoring chip buried in the concrete via a radio interface or the antenna and reads various measurement data related to the quality of the concrete and stored in a memory in the monitoring chip according to the invention as described later. The inspection device RC1 judges the quality of the concrete according to a quality judgment program (QPR1) stored in the secondary storage HDD1 or in the memory MEM1 based upon received measurement data. The inspection device can communicate with the management server (SV10) through a wide-area network (WAN1) represented by the Internet via the network interface (NI1). As described later, when the quality is judged, higher-precision judgment is also enabled, referring to various information (for example, correlation between detection data and the quantity of concrete) stored in a database DB10 in the management server SV10 through the network.

The management server (SV10) specific to the invention is composed of a network interface (NI10), a processor (CPU10), a memory (MEM10) and a database (DB10) formed by a secondary storage. The management server SV10 stores various information (correlation between the result of detection and the quality) required when the quality is judged in the database DB10 and transmits it to the inspection device via the network according to a request from the inspection device RC1 according to the invention. Besides, the management server stores/manages the result of inspection transmitted from the inspection device in the database and can also manage the quality of a remote building. It can be also realized that the quality judgment program is run by the processor CPU 10 in the management server instead of the inspection device RC1 and the result is transmitted back to the inspection device.

Figure 2:
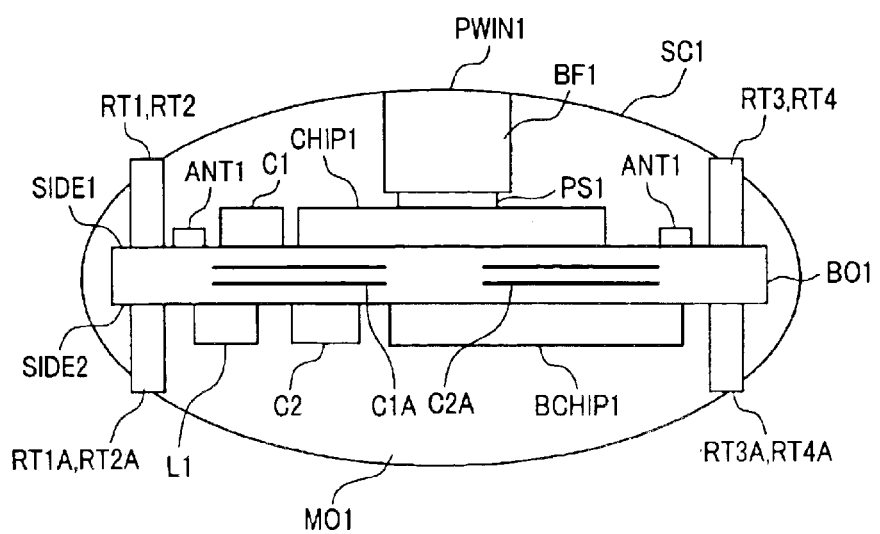
FIG. 2 is a sectional view showing a monitoring chip used in the quality monitoring system for building structure according to the invention.
Figure 3A:
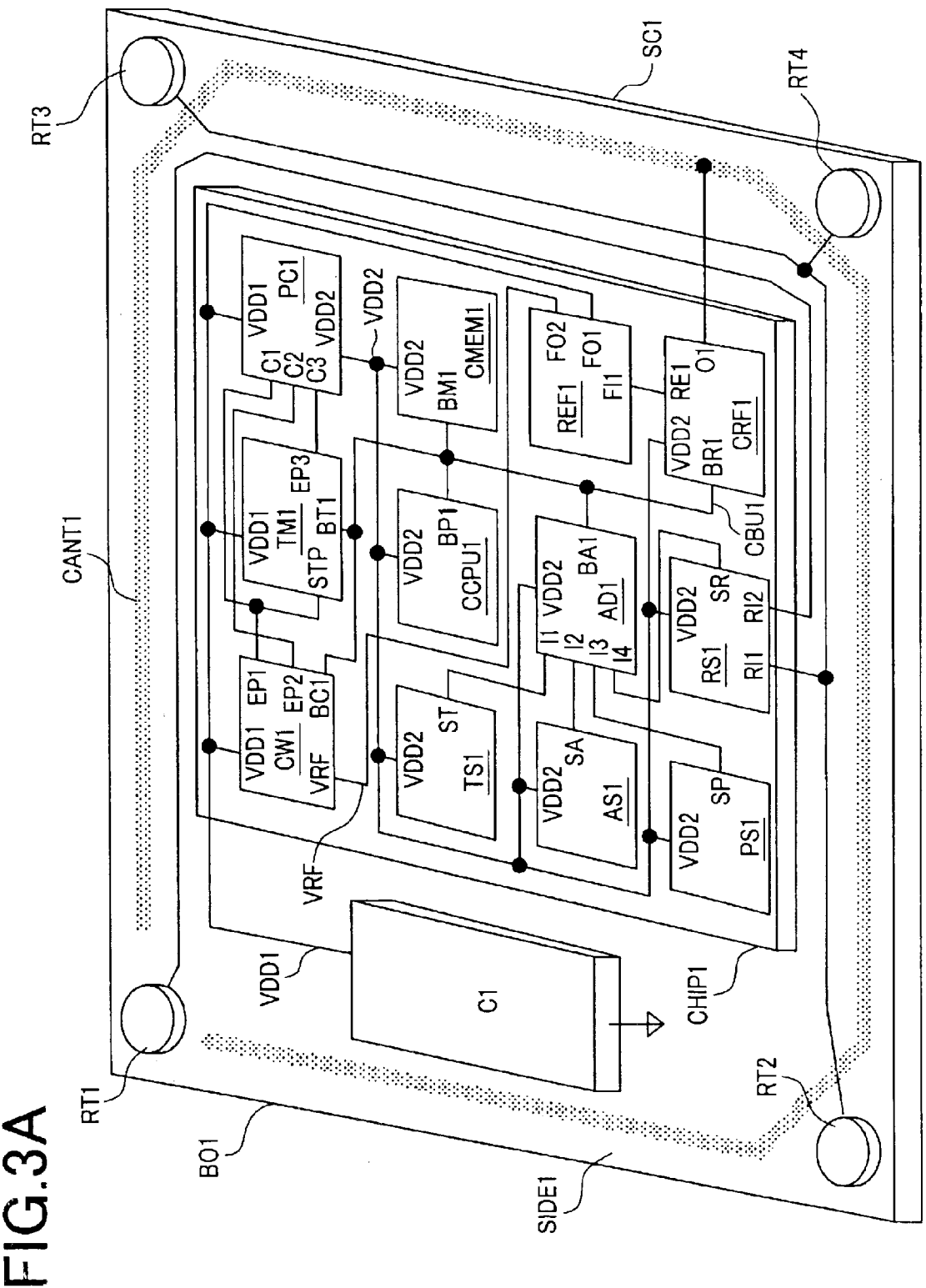
FIG. 3 show the detailed configuration of the monitoring chip according to the invention.
Figure 3B:
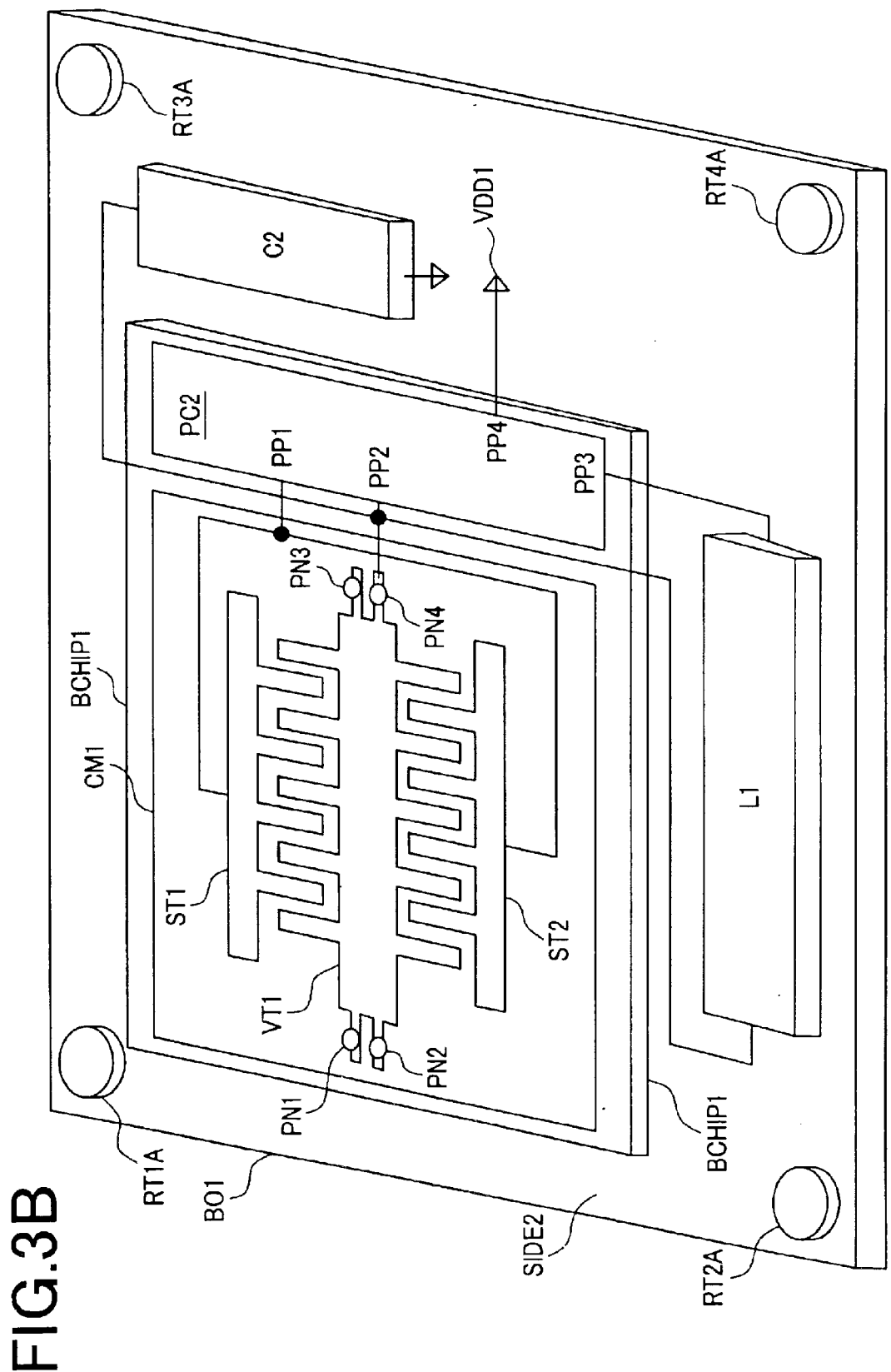

FIG. 2 is a sectional view showing the monitoring chip (SC1) specific to the invention. Further, FIG. 3A shows one main surface (SIDE1) of the monitoring chip SC1. Similarly, FIG. 3B shows the main surface (SIDE2) reverse to the main surface shown in FIG. 3A. As shown in these drawings, the monitoring chip (SC1) specific to the invention is composed of a first semiconductor integrated circuit (CHIP1), a first semiconductor integrated circuit for generating electric power (BCHIP1), capacitors (C1, C2), an inductor (L1) and a substrate (BO1) for mounting them. Of these, on the substrate (BO1), a wiring pattern for connecting these, an antenna (CANT1) pattern used in a radio interface circuit (CRF1) described later and the patterns of electric resistance measurement terminals (RT1 to RT4, RT1A to RT4A) used in an electric resistance sensor circuit (RS1) described later are formed by metal such as copper and gold. These patterns are normally formed by the similar material to the one used in multi chip package (MCP) technique. The similar chip type to the one used in a normal MCP chip can be used for the capacitors (C1, C2) and the inductor (L1). For the capacitor, as shown in FIG. 2, a multilayer substrate is used for the substrate BO1 and some layers are used in pairs. Laminated capacitors (C1A, C2A) can be also utilized.

Further, as shown in FIG. 2, the first semiconductor integrated circuit (CHIP1) and the first semiconductor integrated circuit for generating electric power (BCHIP1) are mounted on the substrate (BO1) in arrangement specific to the invention. That is, CHIP1 and BCHIP1 are mounted not on the same surface of the substrate but on a first substrate surface (SIDE1) and on a second substrate surface (SIDE2).

Besides, as shown in FIG. 2, the semiconductor integrated circuits, the capacitors, the inductor and the substrate are covered with mold material (MO1) such as epoxy resin having a water resisting property and durability. For the mold, the similar material to normal MCP can be used, however, as the monitoring chip according to the invention is mixed in concrete paste as described later and is finally integrally buried in a concrete wall or floor, it is required to be more thickly molded than the thickness when a normal semiconductor integrated circuit is produced. Further, there is a characteristic that a pressure window (PWIN1) specific to the invention is made of mold material BF1 which is material that can transmit pressure from the outside to the inside, slightly reducing the pressure so that a pressure sensor (PS1) mounted on the first semiconductor integrated circuit (CHIP1) inside the mold can detect pressure applied to the inside of concrete.

In the monitoring chip (SC1) according to the invention configured by these semiconductor integrated circuits (CHIP1, BCHIP1), an electric power generator, various sensors such as an electric resistance sensor, the memory, CPU and the radio interface are integrated in one chip as described later. Therefore, the quality of concrete since concrete paste is prepared can be permanently monitored and monitoring the quality of concrete since concrete paste is prepared that determines the quality of concrete building structure, which could not be previously realized, is enabled.

Figure 4:
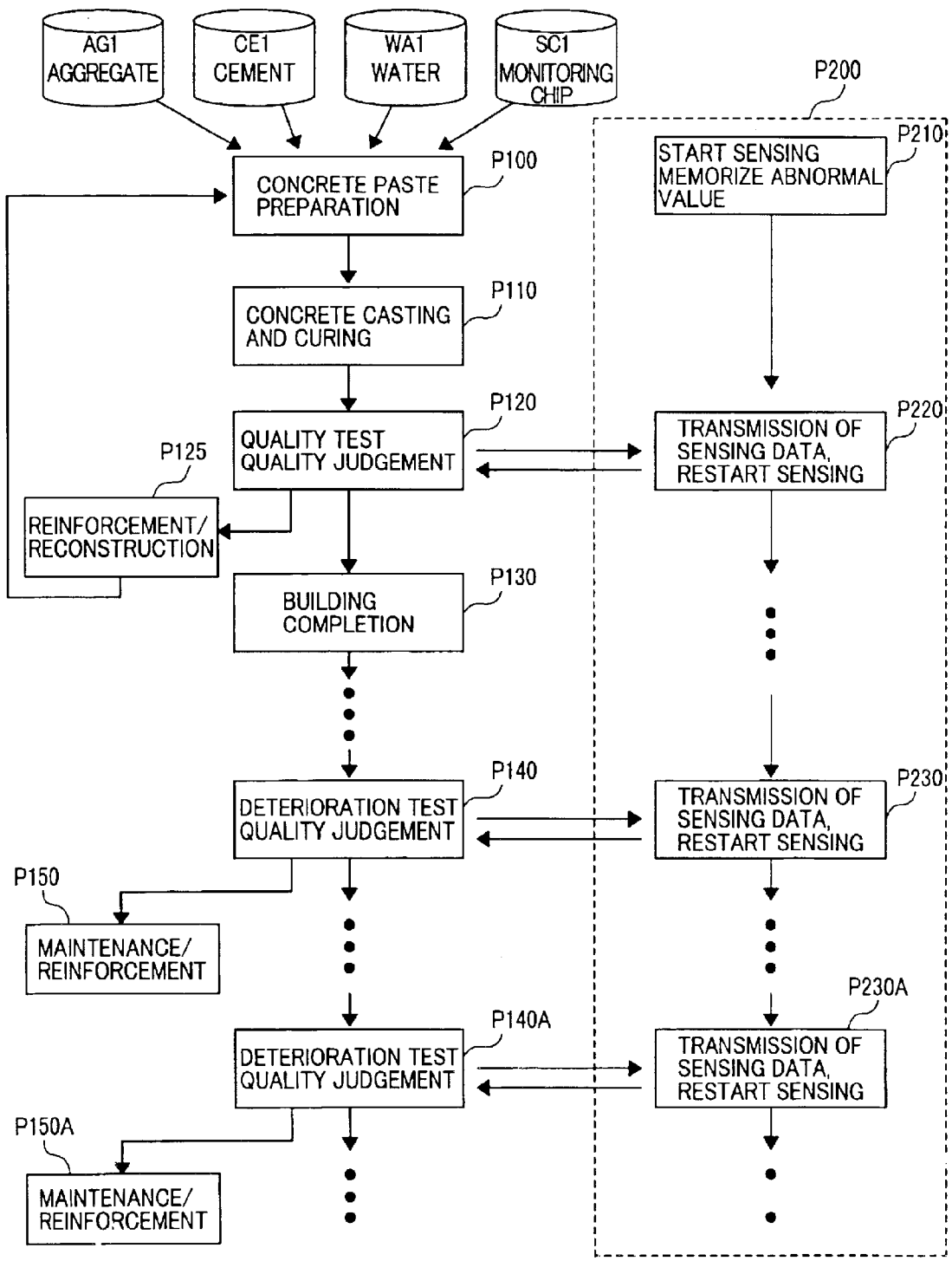
FIG. 4 shows a method of constructing the building structure in which the monitoring chip according to the invention is built and a quality monitoring method for building structure.

FIG. 4 shows a method of constructing building structure and a quality monitoring method respectively specific to the invention which enable monitoring the quality since concrete paste is prepared. As shown in FIG. 4, for a method specific to the invention, a monitoring chip SC specific to the invention is mixed in addition to normal concrete material composed of an aggregate AG1, cement CE1, water WA1 since concrete paste is prepared P100. Though the above-mentioned is described in detail later, the quantity of moisture and the quantity of chloride ions respectively included in concrete are measured without supplying electric power from an external device by the electric power generator, the sensor (the electric resistance sensor, the temperature sensor and others), CPU and the memory respectively built in the monitoring chip according to the invention and it can be permanently monitored whether they are in the ranges of preset allowable values or not. Further, the values of the monitored quantity of moisture and the chloride ions can be transmitted to the inspection device RC1 using the built-in radio interface by radio communication.

In the quality monitoring method for building structure according to the invention shown in FIG. 4, the abovementioned functions specific to the monitoring chip according to the invention are utilized for monitoring the quality of building structure. That is, the monitoring chip starts detecting operation at the same time as the preparation of concrete paste and stores the measured quantity of moisture and other outliers in the memory (P210). Further, the temperature sensor (TS1) built in the monitoring chip monitors whether the change of temperature in curing concrete is in a preset allowable range or not and in case the change of temperature is not in the allowable range, the monitoring chip similarly stores the outlier in the memory (CMEM1) of the monitoring chip. Next, after curing is finished, the inspection device RC1 executes the quality test of concrete (P120). In the test, data in the memory of the monitoring chip is read (P220) according to a request from the inspection device and it is determined whether the quantity of moisture and the density of chloride ions in preparing concrete are adequate or not and whether temperature control in curing is adequate or not. At this time, in case the inadequate quality of concrete is used and in case the control of curing is not enough, they can be immediately detected and in the case of the reinforcement of the corresponding location or in the worst case, partial/whole reconstruction (P125) is enabled at an early stage. That is, the use of inadequate concrete which comes to a head by an accident that concrete in a tunnel flakes can be immediately detected in a check when construction is finished without using the inadequate concrete for the long term of a few years with the concrete left alone. As described above, the monitoring of the quality since the start of the construction of building structure, which could not be heretofore realized is enabled by using the monitoring system, the monitoring method and the monitoring chip respectively specific to the invention and as a result, the high quality of building structure is realized.

The monitoring of the quality when building structure is constructed has been described above, however, as shown in FIG. 4, in the invention, so-called aging change or deterioration since the building structure is completed can be also monitored as in the prior art. For example, the inspection device RC1 is inserted into the building structure once in some years and the similar inspection to inspection when the building structure is constructed is executed (P140). During the period, the monitoring chip built in the building structure also generates electric power in the built-in electric power generator using minute vibration in the building structure as an energy source as described in detail later, continues detecting operation and can detect whether concrete is cracked and rainwater infiltrates the inside for example or not. Further, the distribution of internal stress in the building structure can be detected by totalizing pressure inside concrete measured by the built-in pressure sensor by the individual monitoring chip in the inspection device and checking whether stress fatigue is caused or not is enabled.

The monitoring chip according to the invention can be produced in a semiconductor process in which mass production is enabled. Besides, a high-priced optical fiber sensor described in the prior art is not required. Further, in the invention, when concrete paste is prepared, the monitoring chip according to the invention can be mixed with other materials. Therefore, such construction is enabled at an extremely low-priced additional cost. As described above, not only the quality monitoring system, which could not be realized by the prior art, can be realized but monitoring which can be also realized by the conventional type monitoring system/method can be provided by very low-priced substitutional means.

The outline of the monitoring system, the monitoring method and the monitoring chip according to the invention has been described above, however, the details of the monitoring chip which is the foundation of the invention will be described below. As shown in FIG. 3, the first semiconductor integrated circuit (CHIP1) is composed of a microprocessor (CCPU1), a memory (CMEM1), a radio interface (CRF1), an antenna (CANT1), a rectifier (REF1) that converts high-frequency electric power radiated from an external device via the antenna to D.C. electric power, sensors including a temperature sensor (TS1), an acceleration sensor (AS1), a pressure sensor (PS1) and an electric resistance sensor (RS1), an A/D converter (AD1) that converts an analog signal from the sensor to a digital signal, an electric power controller (PC1) that controls the supply of electric power to CCPU1, CMEM1, CRF1, TS1, AS1, PS1, RS1 and AD1, a timer (TM1) that controls whether PC1 is turned on or not and an electrical charge monitor (CW1) that monitors the quantity of electrical charge stored in the capacitor C1 installed on the substrate BO1 and whether high-frequency electric power is radiated from the external device or not.

The microprocessor CCPU1 sets and controls the operating mode of each circuit on the chip according to a program (PR1) stored in the memory CMEM1, drives each sensor and monitors the quality of concrete. Besides, as described later, the microprocessor transmits detection data to an external device by radio via the radio interface CRF1 after the microprocessor compresses the detection data or executes processing such as adding ID information.

The memory CMEM1 holds abnormal data acquired from the sensor and information such as the parameters of the operating modes for example in the microprocessor CCPU1 in addition to the program PR1. The memory CMEM1 is typically formed by SRAM in which data can be held at low power consumption or a NOR-type or an AND-type flash memory in which the contents of the memory are held even when electric power is turned off. However, it need scarcely be said that another type of memory can be also used if only the contents of the memory can be held at low power consumption.

The first semiconductor integrated circuit for generating electric power (BCHIP1) is a small-sized electric power generator that converts minute extraneous vibration to electric energy. If minute vibrational energy in a floor and a wall is utilized, the power generation of approximately 10 $\mu$W is enabled. The operation of the semiconductor integrated circuit for generating electric power will be described concretely below.

The semiconductor integrated circuit for generating electric power BCHIP1 is composed of a variable capacitor (CM1) the capacitance of which varies depending upon extraneous vibration and an electric energy scavenging circuit (PC2). The electric energy scavenging circuit PC2 scavenges electric energy converted from the mechanical energy of extraneous, vibration by the variable capacitor CM1 and charges the capacitor C1 on the substrate BO1. The variable capacitor CM1 is normally formed with minute structure on a silicon chip in a micro electro mechanical system (MEMS) process. Concretely, as shown in FIG. 3B, the variable capacitor is composed of two fixed electrodes (ST1, ST2) and a movable electrode (VT1). Of these, the movable electrode (VT1) is fixed to nowhere except anchors (PN1 to PN4) and floats over BCHIP1. Therefore, when BCHIP1 is vibrated for example at certain acceleration, it vibrates the two fixed electrodes (ST1, ST2) by inertia force generated hereby. Distance between these electrodes varies by the vibration and the capacitance of the variable capacitor CM1 varies.

Figure 5A:
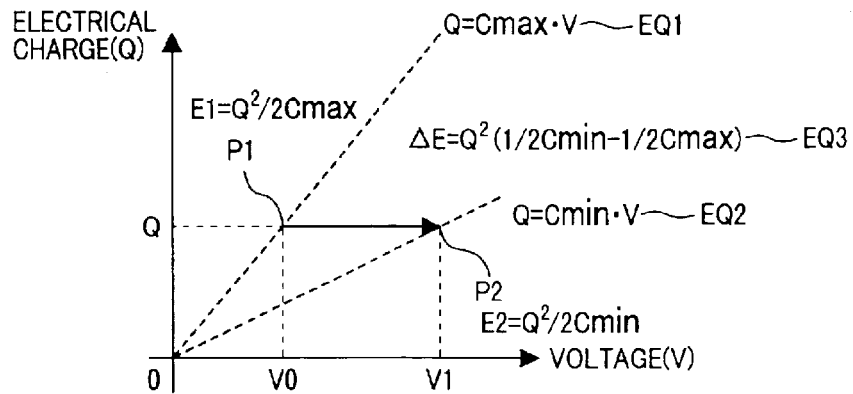
FIG. 5 show the operational principle of a semiconductor integrated circuit for generating electric power mounted on the monitoring chip according to the invention and the configuration and the operation of a circuit for scavenging generated electric power.

FIG. 5A shows the variation of voltage V and electrostatic energy in case the capacitance of CM1 varies from Cmin to Cmax by extraneous vibration when the electrical charge Q of the variable capacitor CM1 is fixed. The capacitance varies by extraneous vibration as described above and as a result, stored electrostatic energy is increased. The function as the small-sized electric power generator is fulfilled by scavenging the increased quantity of the electrostatic energy.

Figure 5B:
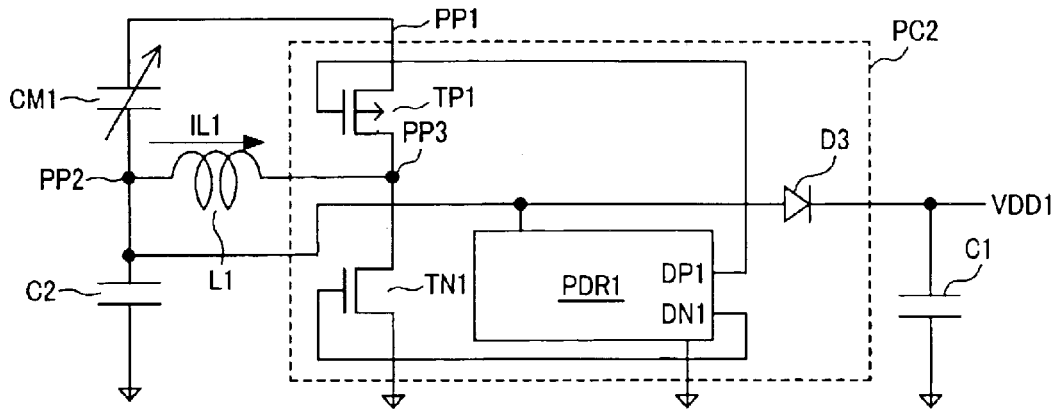
Figure 5C:
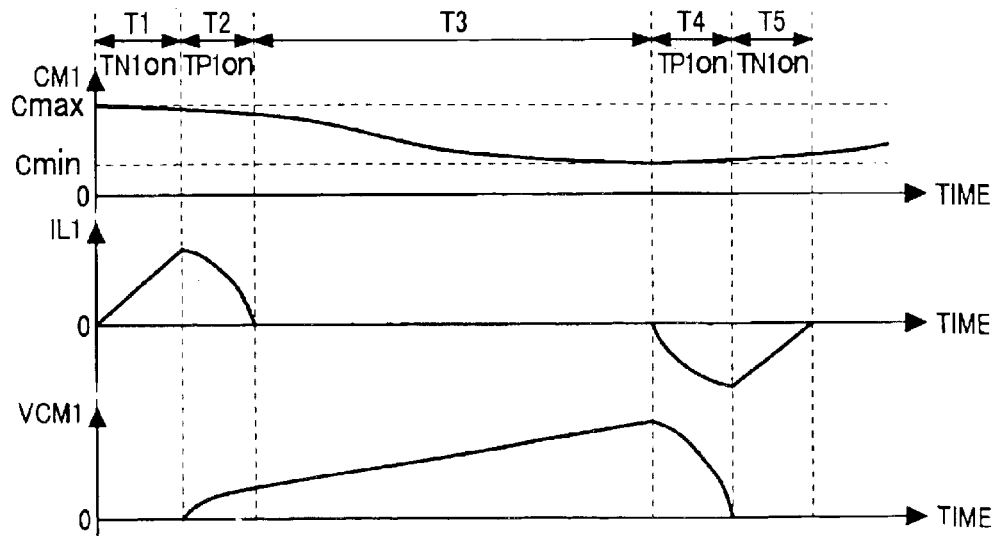

FIG. 5B shows one embodiment of the electric energy scavenging circuit formed on BCHIP1. The similar configuration to that of the conventional type can be used for the electric power generator. The electric power generator is composed of the capacitor C2, the inductor L1 and the electric energy scavenging circuit (PC2) including a rectifier D3, a PMOS transistor TP1, an NMOS transistor TN1 and a driver (PDR1) that controls the timing of when these transistors are turned on or off in addition to the variable capacitor CM1. The driver PDR1 controls the on and off operation of TN1 and TP1 at timing (T1 to T5) shown in FIG. 5C according to the variation of the capacitance of the variable capacitor CM1 by extraneous vibration. As the electric energy scavenging circuit is not a characteristic component of the invention, the description is omitted. Generated electric power is finally supplied to a VDD1 line via the rectifier D3 and is charged in the capacitor C1 connected to the electric power controller PC1 of the first semiconductor integrated circuit CHIP1.

The variable capacitor CM1 can be basically produced in a MEMS process compatible with the semiconductor process. Therefore, the variable capacitor can be also mixed with one semiconductor integrated circuit. However, as shown in FIG. 5A, extracted electric energy depends upon two values of the capacitance (difference between the maximum capacitance Cmax and the minimum capacitance Cmin) of the capacitor CM1 and initial electrical charge Q. That is, the larger the capacitance of the capacitor CM1 is or the larger the initial electrical charge Q is, the larger electric energy can be extracted. Therefore, the capacity the capacitance of which is large is desirable and the capacitor the capacitance of which is approximately a few hundred pF is normally required. To increase capacitance, a groove between the electrodes formed in the shape of a comb is required to be deepened in addition to increasing the area of CM1 shown in FIG. 3B. Therefore, the electrode in the size of approximately 1 cm×1 cm×0.5 mm (depth) is required.

The groove is formed by etching, however, in a normal semiconductor integrated circuit, etching by 0.5 mm is not required. In the meantime, considering the cost when the semiconductor integrated circuit is produced, it is desirable that the area of the capacitor CM1 is smaller. Besides, it is desirable that the groove made by etching is not deep so much.

To solve such a contradictory problem, in the monitoring chip according to the invention, the variable capacitor CM1 and the electric energy scavenging circuit, and the circuits except them are formed in separate semiconductor integrated circuits as shown in FIG. 3. Such separate two chips can be produced in a process dedicated to each chip and the depth of the groove can be also arbitrarily formed. Further, for configuration specific to the invention, these chips are mounted on both sides (SIDE1, SIDE2) of the substrate in MCP. As the area of the variable capacitor CM1 can be increased up to size equal to the size of the sensor chip by such configuration, the variable capacitor having large capacity can be realized. Further, as shown in FIG. 3, the capacitor C2 and the inductor L1 respectively essential as the electric energy scavenging circuit and the antenna CANT1 required for the ratio interface can be mounted in another area of the substrate BO1 or can be formed as a wiring pattern. That is, a sensor system in which the electric power generator, the sensors, CPU and RF are integrated can be realized in the substantially normal size (1 cm square or less) of an IC chip by the configuration shown in FIG. 3 specific to the invention. As a result, a monitoring microchip in which autonomic movement is enabled can be realized.

As described above, the monitoring chip according to the invention can autonomically power off. However, in the prior art, in size approximately 1 cm square, generated electric power is approximately 10 $\mu$W. In the meantime, in a semiconductor integrated circuit produced in a CMOS process, the power consumption of a microprocessor and a memory (Particularly, SRAM) can be reduced up to approximately 10 $\mu$W by reducing a clock frequency up to approximately 100 kHz. In the case of this embodiment, the main processing of the microprocessor is work to an extent that the microprocessor compresses data and stores the data in the memory and can be sufficiently processed at the clock frequency of approximately 100 kHz. For example, even if a clock frequency is set to 100 kHz, the microprocessor can execute instructions 0.1 million cycles per second and can execute approximately 100 instructions in one millisecond. Therefore, electric power is supplied by the above-mentioned electric power generating chip, and the processor, the memory and others can be operated.

However, it is difficult to simultaneously drive various sensors on CHIP1 by the generated electric power of approximately 10 $\mu$W. Further, to communicate with an external device by radio, the electric power of approximately 100 $\mu$W is also required in a radio interface the power consumption of which is very low such as UWB.

Figure 6A:
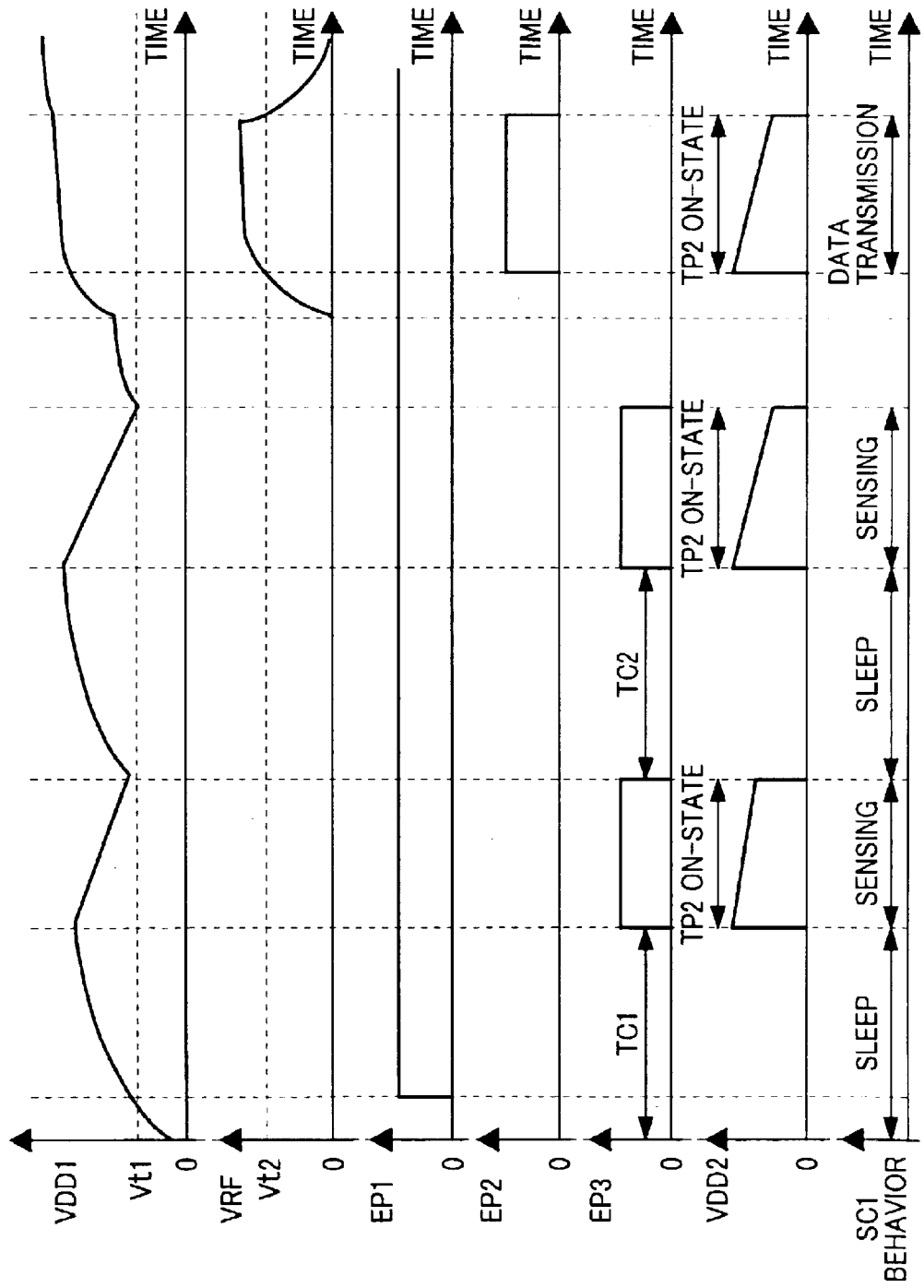
FIG. 6 show the configuration of an electric power controller, a timer and an electrical charge monitor which are a part of the monitoring chip according to the invention.

To solve the problem, in the invention, a low power consumption operated system composed of a capacitor C1, a timer TM1, a switching transistor TP2, an electrical charge monitor CW1, a rectifier REF1 and an electric power controller PC1 is adopted. FIG. 6A more concretely shows the low power consumption operated system. That is, normally, electric power generated by the semiconductor integrated circuit for generating electric power BCHIP1 is not supplied to each circuit of CHIP1 and is stored in the capacitor C1 instead. Only in case it is judged that a time interval set by the timer TM1 elapsed or only in case the electrical charge monitor CW1 judges that sufficient electric power is stored, the switching transistor TP2 in the electric power controller PC1 is made to conduct, electric power is supplied to another circuit such as an on-chip sensor, detecting operation is intermittently executed and if necessary, the result of the detection is stored in the memory CMEM1.

As already described, in the monitoring chip according to the invention, data detected by the inspection device by radio is required to be transmitted and the electric power of a few hundred $\mu$W at the minimum is required. Therefore, in the invention, as shown in FIG. 3A, the antenna CANT1 receives high-frequency electric power radiated from the inspection device RC1, the rectifier REF1 converts it to D.C. electric power, and the capacitor C1 stores it to be electric power for transmitting detection data by radio. As described above, the quality of building structure is permanently monitored by adopting the following hybrid system without the supply of electric power from the external device and data can be transmitted according to a request from the inspection device.

1) Detecting operation is executed using electric power from the built-in generator.

2) High-frequency electric power supplied from the inspection device is used for the radio transmission of detection data.

Figure 6B:
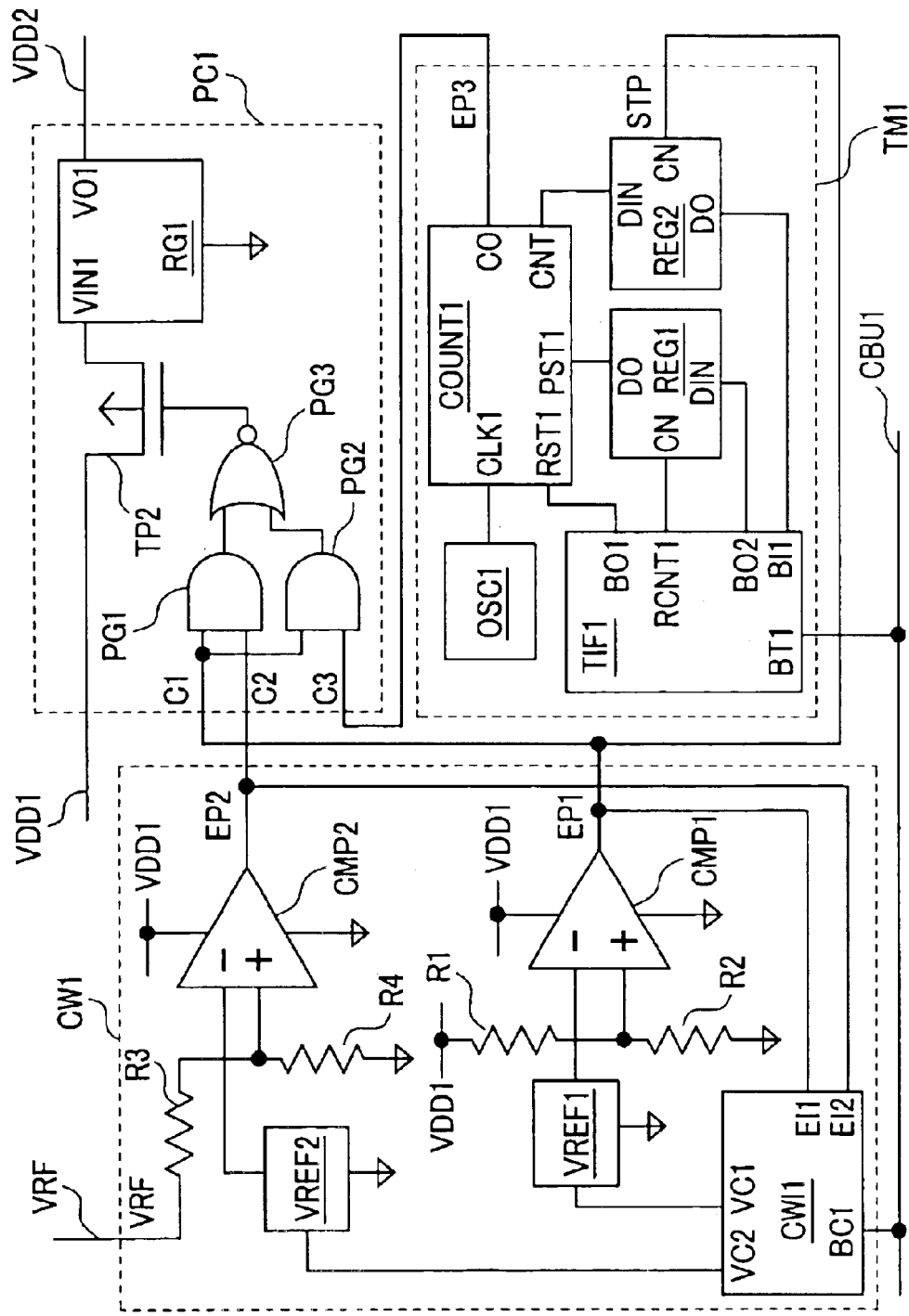

FIG. 6B shows an example of the concrete configuration of the electric power controller PC1 specific to the invention, the electrical charge monitor CW1 and the timer TM1 respectively used for electric power control. As shown in FIG. 6B, the electric power controller PC1 is composed of control theoretical circuits PG1 to PG3 and the switching transistor TP2. In case a signal EP1 from the electrical charge monitor CW1 or the timer TM1 and EP3 are at a high level or in case the electric power monitor judges that high-frequency electric power is supplied from the inspection device, the output of the control theoretical circuit PG3 is turned to a low level, the switching transistor TP2 is made to conduct and electric power is supplied to a VDD2 line. As a result, the memory CMEM1, the radio interface CRF1, the A/D converter AD1, the sensor and other circuits which respectively receive electric power from the VDD2 line are activated. In FIG. 6B, a pressure rising/falling regulator (RG1) is shown, however, as it is not peculiar to the invention, the description is omitted.

The electrical charge monitor CW1 is composed of resistors R1, R2, R3, R4, reference voltage generators VREF1, VREF2, voltage comparators COMP1, COMP2 and a bus interface CWI1 controlled by CCPU1 via a bus CBU1. The electrical charge of the capacitor C1, that is, the voltage of the first power line VDD1 is monitored by COMP1, R1, R2 and VREF1 of these. That is, it is compared with threshold voltage Vt1 expressed by the following expression and in the case of VDD1>Vt1, output EP1 is pulled up to a high level.

$$Vt1 = VR0 \cdot (1 + R1/R2) \quad \text{[Mathematical expression 1]}$$

Similarly, high-frequency electric power is radiated from the external inspection device by monitoring VRF of a signal from the rectifier (REF1) in the residual COMP2, R3, R4 and VREF2 and it is determined whether the transmission of detection data is requested or not. That is, VRF is compared with threshold voltage Vt2 expressed by a mathematical expression 2 and in the case of VRF>Vt2, output EP2 is pulled up to a high level.

$$Vt2 = VR1 \cdot (1 + R3/R4) \quad \text{[Mathematical expression 2]}$$

The values of reference voltage VR0 and VR1 can be also changed from CCPU1 via a bus interface CWIF1. It is stored in a register in CWI1 whether VRF is a set value or more or not and when CCPU1 reads the contents of the register via a bus, it can be checked whether a request is made by the inspection device RC1 or not.

As electric power is constantly supplied to VREF1, VREF2, COMP1 and COMP2, it is desirable that the resistors R1 to R4 for example are designed so that they have a large resistance value (a few tens MΩ or more). These are generally formed in the CMOS process.

The timer TM1 is composed of an oscillator OSC1, a preset counter COUNT1, a register REG1 that holds a preset value of COUNT1, a register REG2 that holds a count value until the electrical charge monitor CW1 reaches defined voltage and a bus interface TIF1 with CCPU1. The preset counter COUNT1 counts up to the present value set in the register REG1 and outputs a high-level signal to an output line EP3. The contents of the registers REG1 and REG2 are can be written or read to/from CCPU1 via the bus interface TIF1. The values of these registers are set in a routine P330 shown in FIG. 7. As these circuits are not specific to the invention, the description of the details is omitted. As the timer is also constantly energized, the power consumption is required to be reduced. It is suitable for the reduction of power consumption to set the oscillation frequency of the oscillator OSC1 to a small value. Typically, current consumed by the timer TM1 can be reduced up to 1 μA or less by setting the oscillation frequency to approximately 32 kHz.

An operational system specific to the invention that the other most circuits of the semiconductor integrated circuit CHIP1 are not operated normally, are energized only for a short time, intermittently detect and only in case high-frequency electric power is transmitted from the external inspection device, the circuits transmit data to the inspection device is realized by PC1, CW1, TM1. The above-mentioned problem of electric power can be also solved by such intermittent operation. For example, the capacitor C1 of approximately 1 μF can be typically used and when the capacitor is charged up to 1 V, electrical charge of 1 μC can be stored. In other words, 1 mA can be extracted for one second using the capacitor as a power source. That is, the capacitor can operate a circuit the power consumption of which is approximately 1 mW. In the meantime, when electric power generated by the generating chip is 10 μW (to voltage 1V), time expressed by the following expression is required to charge by 1 μC.

$$1 \mu C/(0.01/1 \ mA) = 1000 \ msec \quad \text{[Mathematical expression 3]}$$

Even if it takes 2 seconds to charge, the chip can be driven approximately 5 times in 10 seconds and the sensor can be driven with the power consumption of 1 mW. In the case of monitoring the quality of building structure as in this embodiment, even approximately once per hour as the shortest time interval of monitoring is enough. It is known that time required for curing concrete is approximately one month. Therefore, even if monitoring operation is intermittently executed at an interval of a few seconds as in the invention, nothing is hindered practically. Further, as already realized in an IC card, it is validated that a high frequency is radiated from an external device and electric power of approximately a few mW can be continuously supplied. As described above, in the sensor chip according to the invention, a hybrid electric power supply system that high-frequency electric power is supplied from a micro electric power generator produced in an MEMS process or from the external inspection device via an antenna is enabled by the electric power controller specific to the invention, the quality of building structure is autonomically monitored without a battery and data can be transmitted to the inspection device by radio.

Figure 7A:
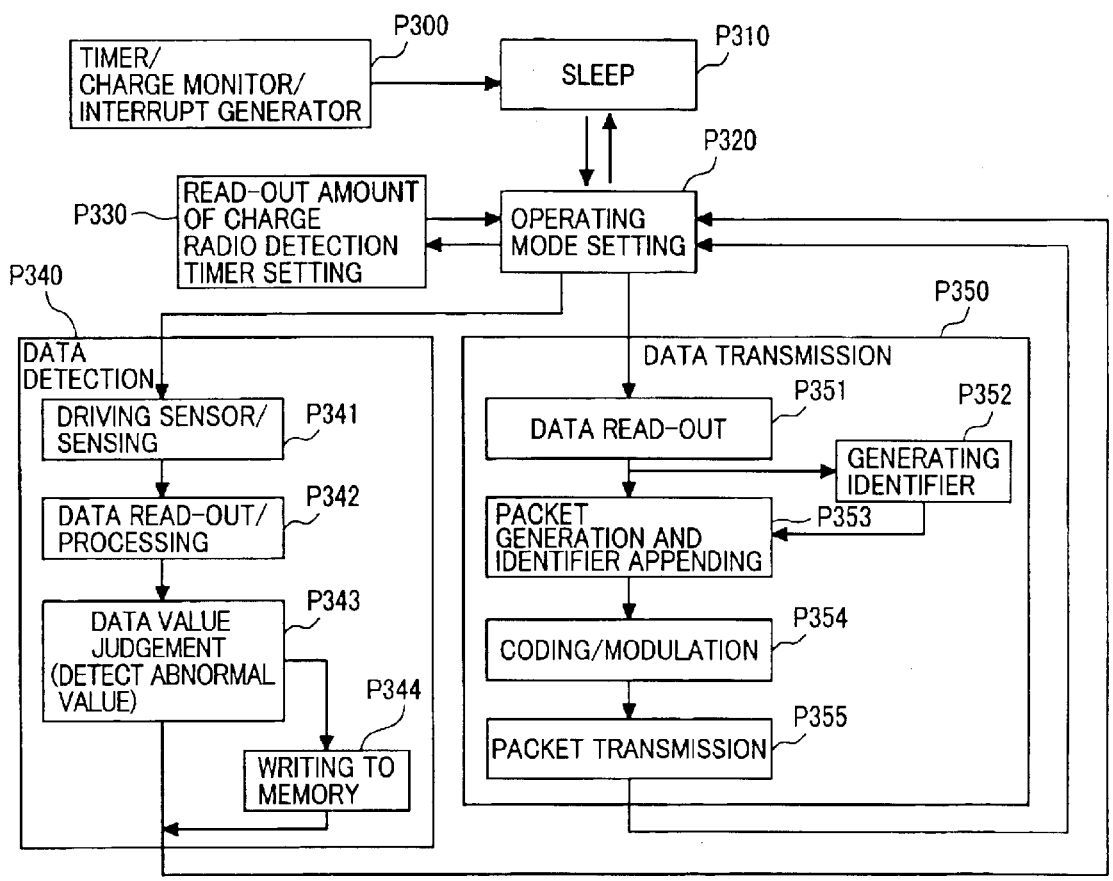
FIG. 7 show the outline of the operation of the quality monitoring chip for building structure according to the invention and the outline of transmitted data.

FIG. 7A is a flowchart showing the operation realized according to the above-mentioned electric power control system of the monitoring chip according to the invention. As shown in FIG. 7A, CCPU1 is always in a sleep state P310. The sleep state proceeds to an operated state in P320 or later by an interrupt from the timer TM1 or the electrical charge monitor CW1. In the operated state, the succeeding operation is determined according to a problem stored in the memory CMEM1 or an operational parameter. For example, if the operational parameter is the detection of data, a data detection routine P340 is called, a sensor driving/sensing subroutine P341, a data read-out/processing (compression) subroutine P342 and a data value judgment subroutine P343 are sequentially executed, data is acquired from the sensor, it is determined whether the acquired data is data in a preset range or not and in the case of an abnormal value, the data is written to the memory. In the meantime, in case it is detected in the electrical charge monitor CW1 that high-frequency electric power is radiated from the external inspection device and it is judged that the transmission of detection data is requested, a data transmission routine P350 is called, data stored in the memory is read by a data read-out subroutine P351, if necessary, an identifier generation subroutine P352, a packet generation subroutine P353, a coding/modulation subroutine P354 and a packet transmission subroutine P355 are sequentially executed and data is transmitted.

Figure 7B:
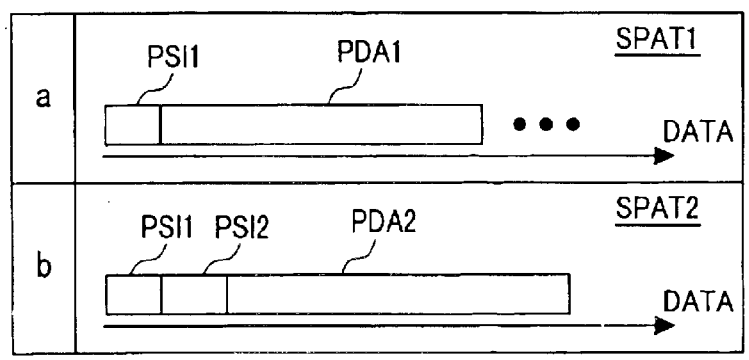

Data to be transmitted is transmitted in the form of a packet (SPAT1) composed of an identifier (PSI1) and data (PDA1) as shown in a of FIG. 7B. As described above, even if the plural monitoring chips according to the invention are simultaneously used, the inspection device RC1 can discriminate which monitoring chip transmits the corresponding data by appending an identifier to transmitted data. For the identifier PSI1, typically, information proper to the chip such as proper ID written to a nonvolatile memory part of the memory CMEM1 when the semiconductor integrated circuit CHIP1 is shipped can be used. Further, as shown in b of FIG. 7B, in addition to the identifier PSI1, the identification information (the type of a sensor PSI2) of from which sensor of the monitoring chip the corresponding information comes for example can be also appended. In an operating mode setting routine P320, a state in which the electrical charge monitor CW1 is charged is read from a register CR1 recording the state or is written to a time interval setting register TR1 of the timer TM1. Hereby, the setting of operation in accordance with a situation in which the semiconductor integrated circuit for generating electric power BCHIP1 generates electric power is enabled.

FIG. 8 show the configuration of various sensors mounted on the first semiconductor integrated circuit of the monitoring chip according to the invention.

Figure 8A:
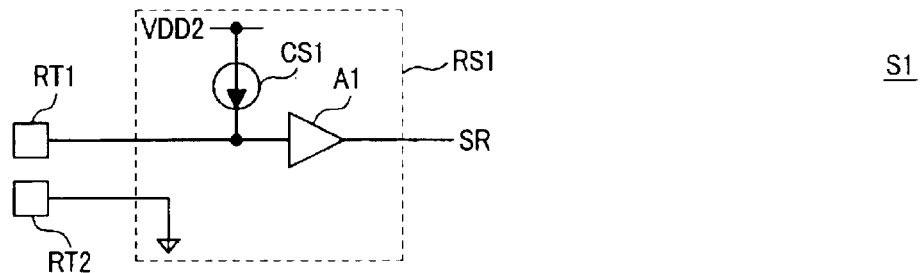
FIG. 8 show the configuration of an electric resistance sensor, a temperature sensor, an acceleration sensor and a pressure sensor which are a part of the monitoring chip according to the invention.

FIG. 8A shows an example of the configuration of the electric resistance sensor RS1. A voltage drop between electrodes RT1, RT2, RT3, RT4 respectively provided outside is measured by a constant current source CS1 and an amplifier A1. Electric resistance/Impedance between the two electrodes can be measured by dividing the measured voltage drop by a current value set to the constant current source CS1. It need scarcely be said that the electric resistance sensor shown in FIG. 8A is one example of the configuration of the electric resistance sensor and the sensor having another configuration can be also used (the following sensors are also similar).

Electric resistance in concrete can be measured by the electric resistance sensor and a corrosion rate of concrete can be measured based upon the electric resistance. Further, as moisture and salinity (a chloride ion) in concrete have electric conductivity, it can be measured by mixing the monitoring chip and measuring electric resistance since concrete paste is prepared as shown in P210 or later of the flowchart shown in FIG. 4 whether an amount of moisture in concrete paste is too much or not or whether inadequate material such as a chloride ion is used or not. Further, if the operating program shown in FIG. 7 of the monitoring chip is suitably set and abnormal values since mixing are stored in the memory, it can be detected by reading the abnormal values in the inspection device later whether inadequate concrete is used in preparation or not.

Figure 8B:
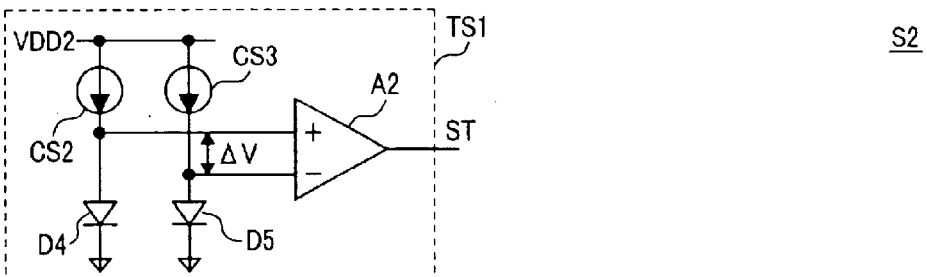

FIG. 8B shows an example of the configuration of the temperature sensor used in the monitoring chip according to the invention. As shown in FIG. 8B, the temperature sensor is composed of diodes D4, D5, constant current circuits CS2, CS3 set to different current values and an amplifier A2. As the temperature sensor of this type is not specific to the invention, the description of the details is omitted. This sensor chip is very small-sized (typically, 5 mm square or less) and the heat capacity of the chip itself is an ignorable value, compared with a concrete wall or floor. Further, as the power consumption of this sensor chip is very little, the heat of the chip itself can be ignored. Therefore, if the sensor chip is buried in concrete in the form shown in FIG. 1, the temperature of concrete can be precisely measured by this temperature sensor.

The variation of the temperature in curing after concrete is cast is monitored by this temperature sensor and can be stored in the memory. As in the above-mentioned electric resistance sensor, the variation of the temperature during curing can be read in the inspection device later. That is, though it was heretofore impossible to realize, it can be detected by using this monitoring chip whether inadequate management is made during curing which plays an important role to strengthen concrete or not.

Figure 8C:
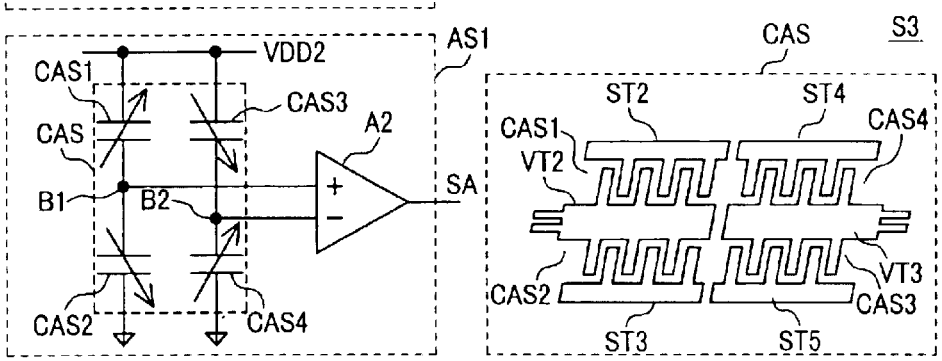

FIG. 8C shows an example of the configuration of the acceleration sensor AS1. The acceleration sensor is composed of variable capacitors CAS1 to CAS4 produced in an MEMS process and a differential amplifier A3. The variable capacitor basically has the same structure as the capacitor for power generation CM1 formed on the semiconductor integrated circuit for generating electric power BCHIP1. Like CM1 shown in FIG. 3B, the capacitance of CAS1 to CAS4 varies because distance between the movable electrode and the fixed electrode varies by inertia force generated by acceleration. For example, when acceleration is generated downward from the surface of paper space in FIG. 8C, the movable electrodes VT2 and VT3 are moved upward from the surface of the paper space. Therefore, the capacitance of CAS1 and CAS3 increases and the capacitance of CAS2 and CAS4 decreases. Therefore, though the potential of B1 rises, the potential of B2 conversely falls. As a result, the output potential of the differential amplifier A2 rises and it can be detected that acceleration is applied. As described above, as a relative value of the variation of the capacitance is important in the acceleration sensor differently from the variable capacitor CM1 used on the semiconductor integrated circuit for generating electric power BCHIP1, large capacitance is not required. Therefore, the acceleration sensor can be integrated on the same semiconductor integrated circuit as the processor and other circuits. Detected potential difference is not necessarily linear with applied acceleration. Therefore, after the detected potential difference is read in the microprocessor CCPU1 via the A/D converter described later for example, it is required to be corrected in software in CCPU1. In such a case, it is suitable that a correction table is stored in the memory CMEM1.

A direction of gravity can be detected by using this acceleration sensor and separating a D.C. component of acceleration in CCPU1 for example. Further, three-dimensional acceleration is measured by using two acceleration sensors in orthogonal directions (X Y directions) and further, also forming in a vertical direction of the chip. That is, it can be grasped that at which angle this monitoring chip is installed inside concrete (a wall and a floor). This is necessary information when stress distribution applied to the inside of concrete is calculated as described later.

Figure 8D:
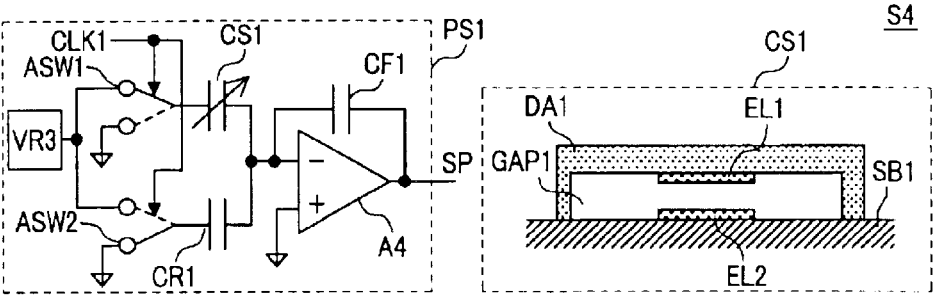
Figure 8E:
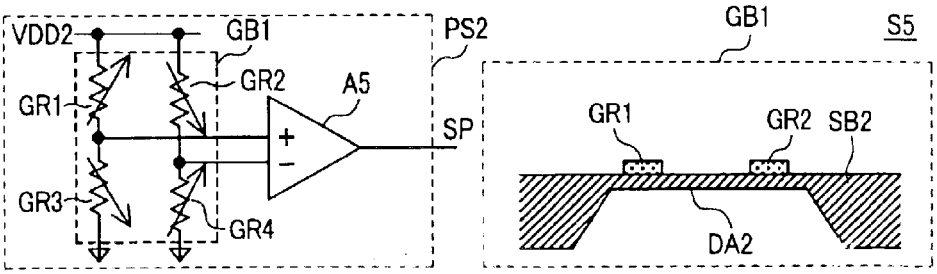

FIGS. 8D and 8E show examples of the configuration of the pressure sensor PS1. Of these, FIG. 8D shows an example of the configuration of the capacitance-type pressure sensor and the capacitance-type pressure sensor is composed of a reference voltage generator VR3, analog switches ASW1, ASW2, an amplifier A4, an integrating capacitor CF1, a pressure sensitive capacitor CS1 and a reference capacitor CR1. The pressure sensitive capacitor CS1 is formed by a diaphragm DA1 which is deflected by pressure and inside which a hollow gap (GAP1) is formed on a semiconductor integrated circuit substrate SB1 as shown on the right side of FIG. 8D by micro processing technique such as MEMS and opposite electrodes EL1, EL2 formed on both sides of the hollow gap GAP1. As this pressure sensor basically has the same structure as the conventional type, the detailed description of the operation is omitted. Voltage linearly proportional to pressure can be acquired by the output of the amplifier A4 in principle by such circuit configuration.

In the meantime, FIG. 8E shows an example of the configuration of a semiconductor strain gauge-type pressure sensor. A diaphragm (DA2) deflected by pressure is formed inside a substrate SB2 itself of a semiconductor integrated circuit by etching and strain gauge resistors (GR1 to GR4) made of polysilicon are formed on DA2. A bridge circuit and an amplifier A5 formed by GR1 to GR4 detect the variation of the resistance values of the strain gauge resistors caused by the deflection by pressure of the diaphragm DA2 and measure the pressure. As this type of pressure sensor is also not specific to the invention, the description of the operation is omitted.

As described above, the above-mentioned pressure sensors can measure pressure applied to the outside of the monitoring chip via the pressure window PWIN1 (see FIG. 2). Stress distribution inside concrete can be measured by using the pressure sensors, the acceleration sensor and positional detection utilizing a radio electric wave described later and further, totalizing information detected by multiple monitoring chips buried inside the concrete.

To input the output of each sensor to the processor, judge whether it is an abnormal value or not, store it in the memory and further, transmit it to an external device by radio as the output of each sensor is an analog value, the output of each sensor is required to be converted to a digital value. Conversion from an analog value to a digital value is realized if only an A/D converter is connected to the output terminal of each sensor, however, it is not desirable in the area and the power consumption of the chip that plural A/D converters are installed. Therefore, it is preferable that an A/D converter shown in FIG. 9 collectively converts to a digital value.

Figure 9:
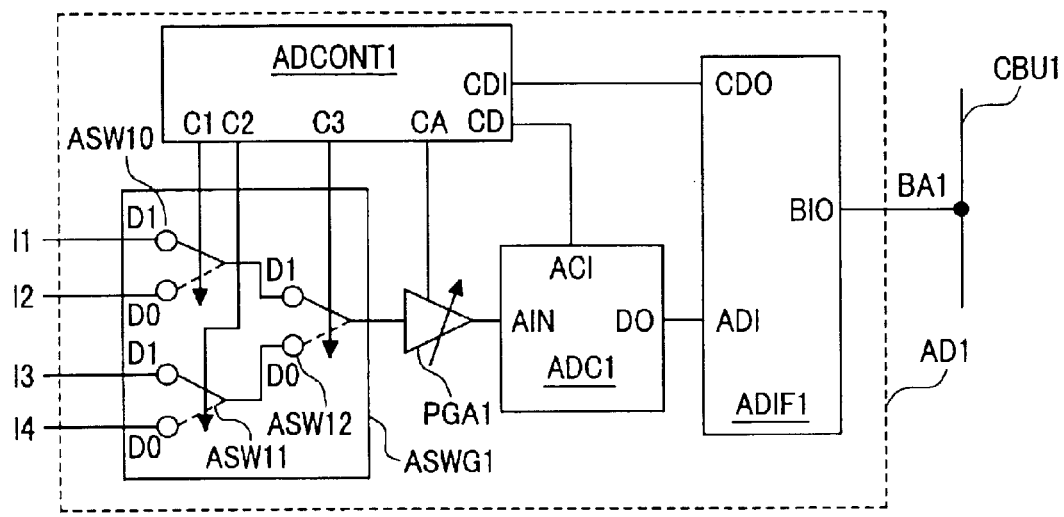
FIG. 9 shows the configuration of an A/D converter provided with a select function which is a part of the monitoring chip according to the invention.

As shown in FIG. 9, the A/D converter (AD1) mounted in the monitoring chip according to the invention is composed of a bus interface ADIF1, ADC1 which is the body of the A/D converter, an input switch ASWG1 formed by analog switches ASW10 to ASW12, a programmable gain control amplifier PGA1 and an A/D conversion controller ADCONT1 that sets the operational parameters of these circuits. The input switch ASWG1 and the programmable gain control amplifier PGA1 set an operational parameter in the controller ADCONT1 according to a control command transmitted from CCPU1 via the bus CBU1.

In case electric resistance is measured for example, CCPU1 sets a control register in ADCONT1 via the bus CBU1 prior to measurement so that the input switch ASWG1 selects I4 (ASW11: D0, ASW12: D0) and the set gain of the programmable gain control amplifier PGA1 is equal to the gain of the electric resistance sensor. The output SR of the electric resistance sensor PS1 is input to the A/D converter via PGA1 by setting as described above, the A/D converter converts an analog value to a digital value and the digital value is input to CCPU1 via the bus interface ADIF1. Similarly, in case the output of another sensor is to be read, the setting of gain in accordance with the sensor and the setting of the input switch are written to the control register in ADCONT1 and ADC1 is driven. Not only the circuit size of the semiconductor integrated circuit CHIP1 can be inhibited by such configuration but the increase of power consumption can be inhibited. For the analog switches ASW10 to ASW12, general analog switches can be used if only they can pass an analog signal without loss. In this monitoring chip, as information to be monitored is limited to a thing that relatively slowly changes such as temperature and electric resistance inside concrete as described above, a slow type is suitable for the A/D converter ADC1.

Figure 10A:
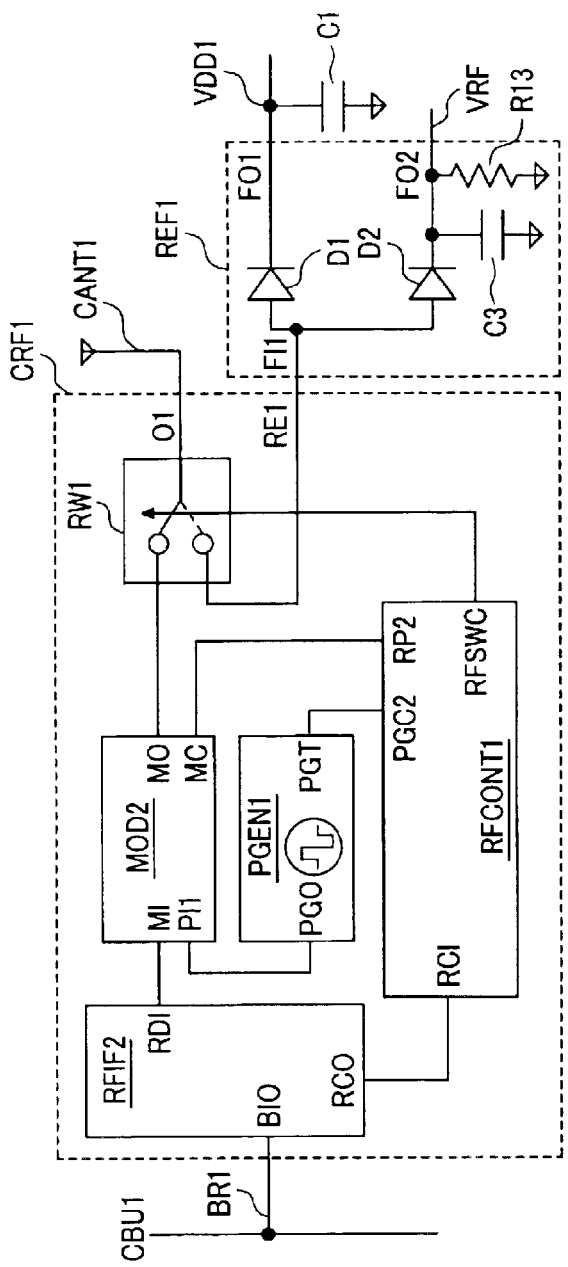
FIG. 10 show the configuration of a radio interface and a rectifier which are a part of the monitoring chip according to the invention.
Figure 10B:
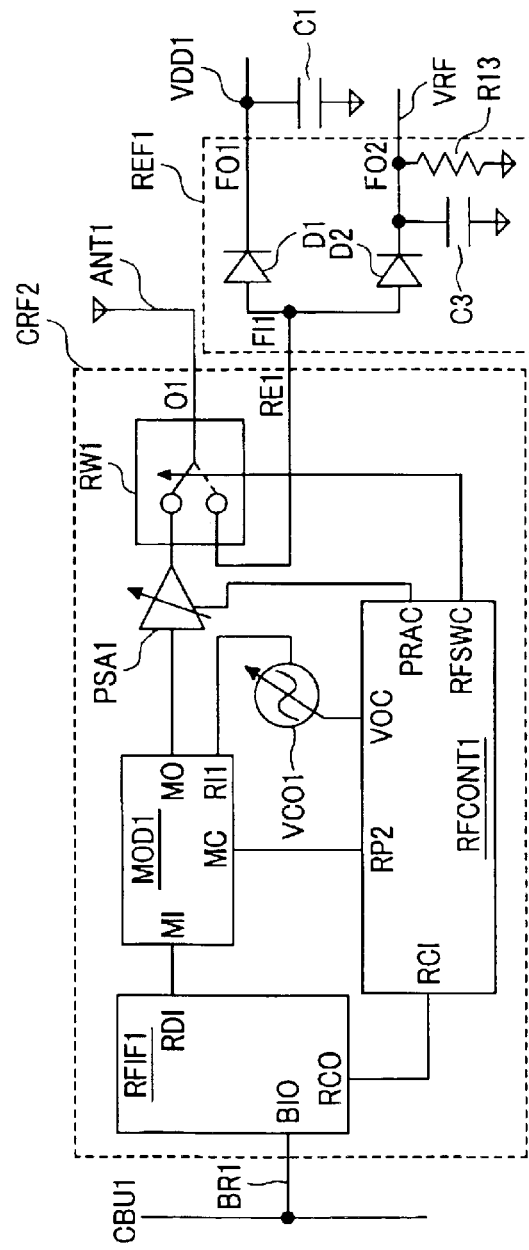

FIGS. 10A and 10B show examples of the configuration of the radio interface CRF1, the antenna CANT1 and the rectifier REF1 in the monitoring chip according to the invention and connection among them. FIG. 10A shows the example of the configuration using an ultra wide band (UWB) telecommunication system. The radio interface is composed of an antenna switch RW1, a bus interface RFIF1, a modulator MOD1 used for transmission, a pulse generator PGEN1 and a controller RFCONT1 that controls the operational parameters of these circuits according to the contents of the control register set by CCPU1 via the bus interface RFIF1. Concretely, the antenna switch RW1 is normally connected from the antenna CANT1 to REF1 and is set so that high-frequency transmission is disabled. In this state, only in case the external inspection device RC1 requests reading and high-frequency electric power is radiated, the high-frequency electric power is converted to D.C. one in a rectifying circuit D1 in the rectifier REF1 and is charged in a capacitor C1. When charging is completed in short time, a seizing signal is output from the electrical charge monitor CW1 to the electric power controller PC1 and each circuit of the semiconductor integrated circuit CHIP1 is activated. Simultaneously, a VRF line connected to a rectifying circuit D2 is also charged and it is detected by the electrical charge monitor CW1 that the external inspection device requested reading. The data transmission routine P350 shown in FIG. 7 is activated by the above-mentioned procedure. A smoothing capacitor C3 for the VRF line is built in the rectifier TEF1. As this capacitor has only to detect whether a radio frequency is radiated or not, the capacitor of small capacity can be used and can be integrated in the first semiconductor integrated circuit CHIP1.

Though the following is not specially shown in the drawing, it is also possible that high-frequency electric power radiated from the inspection device RC1 is modulated according to amplitude shift keying (ASK) for example, a signal is superimposed on the high-frequency electric power, it is demodulated in the rectifier REF1 mounted in the monitoring chip SC1, the signal is extracted and received. If this mechanism is applied, a control signal can be transmitted from the inspection device RC1 to the monitoring chip SC1. Typically, a time interval of the detecting operation of the monitoring chip can be controlled or the other operational parameters can be controlled.

In the data transmission routine P350, CCPU1 sets a register in the controller RFCONT1 via the bus CBU1, switches the antenna switch RW1 to the output terminal of the modulator MOD1 and further, sequentially sends data to the modulator MOD1 via the bus CBU1. The antenna switch RW1 can be formed by a semiconductor device such as a pin diode or a microcontact produced on the surface of a semiconductor chip in an MEMS process and the connection of an RF signal can be switched by controlling the bias voltage of the pin diode or the MEMS microcontact. As these are not specific to the invention, the detailed description is omitted.

In the UWB telecommunication system, no carrier wave is used, a high-frequency pulse signal itself is modulated and data is transmitted/received. For example, a pulse train is modulated to transmit data by transmitting the pulse when data to be transmitted is '1', the pulse and delaying and transmitting the pulse by 100 psec when data to be transmitted is '0'. Therefore, as shown in FIG. 10A, an oscillation and an amplifier required to generate a carrier wave are not required, and only a pulse generator PGEN1 for generating a high-frequency pulse and the modulator MOD1 for controlling whether the pulse is to be transmitted or not are required. That is, a transmit amplifier is not required and the scale of a high-frequency transmitter circuit can be inhibited. As a result, the manufacturing cost of the semiconductor integrated circuit CHIP1 can be inhibited and simultaneously, the reduction of the power consumption can be also realized.

Further, in the UWB telecommunication system, in case only relatively short communication distance is required, RF transmission electric power can be inhibited. In the application of the monitoring chip according to the invention, distance from the monitoring chip buried inside a concrete wall to the inspection device for example is typically approximately 1 m. Therefore, RF transmission electric power can be also set to approximately 10 $\mu$W. As described above, in the UWB telecommunication system, radio communication of ultralow power consumption can be realized and is a desirable telecommunication system for the quality monitoring system for building structure according to the invention.

Figure 11:
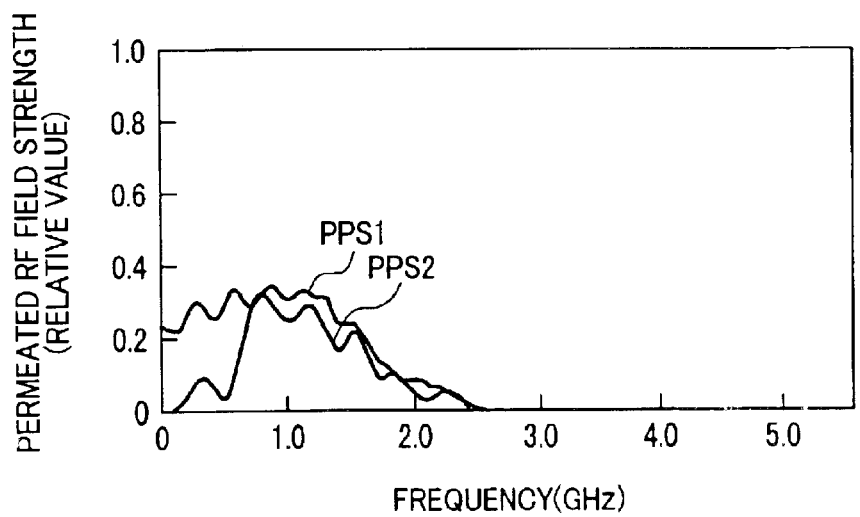
FIG. 11 shows the transmission characteristic of an electromagnetic wave inside concrete.

Further, for the speciality of the invention, it can be given that the frequency band of a UWB pulse is approximately 2 GHz. FIG. 11 shows an example of an electromagnetic wave transmission characteristic in concrete. The electromagnetic wave transmission characteristic in concrete depends upon 1) the thickness of the concrete and 2) whether steel structure exists in the concrete or not, however, basically, a high frequency exceeding 3 GHz has a property that hardly transmits an electromagnetic wave. Therefore, to securely execute radio communication without unsent data, it is practically essential to suit a frequency band used for radio communication to the physical characteristic of concrete. As described above, the reading of data from the monitoring chip buried inside concrete is enabled by utilizing the UWB transmitter circuit specific to the invention the used frequency band of which is suited to the electromagnetic wave transmission characteristic of concrete.

As described above, the UWB telecommunication system is an optimum radiocommunication system for the monitoring chip according to the invention. However, currently, the telecommunication system is not formally authorized in many courtiers including Japan. The telecommunication system will be authorized in future, however, currently, another radiocommunication system is required to be temporarily used. It is a second radio interface for the monitoring chip according to the invention shown in FIG. 10B that is configured for the object. As shown in FIG. 10B, the radio interface is composed of an antenna switch RW1, a bus interface RFIF1, a modulator MOD1 used for transmission, an oscillator VCO1, a transmit amplifier PSA1 and a controller RFCONT1 that controls the operational parameters of these circuits according to the contents of a control register set by CCPU1 via the interface RFIF1. As these circuits are not specific to the invention, the detailed description is omitted, however, as in the circuit shown in FIG. 10A, in case data transmission is requested, CCPU1 sets the control register in RFCONT1 to a transmission mode and sends transmit data to the modulator MOD1 via the bus interface. MOD1 modulates a carrier wave generated by the oscillator VCO1 based upon the sent data. For a modulation mode, various modes such as phase shift keying (PSK) and quadrature amplitude modulation (QAM) can be applied, however, as they are not specific to the invention, the detailed description is omitted. As described above, detection data is superimposed on the carrier wave and is transmitted to the inspection device via the antenna switch RW1.

As shown in FIG. 10B, in the transmitter circuit according to this system, the transmit amplifier and the oscillator are required. Therefore, the scale of the transmitter circuit according to this system is larger than that of the transmitter circuit in the UWB telecommunication system shown in FIG. 10A. Further, for transmitting electric power, for example, approximately 100 $\mu$W is required. Therefore, the power consumption is larger than that of the transmitter circuit in the UWB telecommunication system. However, as already described, in the monitoring chip according to the invention, high-frequency electric power from the external inspection device RC1 is used for electric power for transmitting data. Therefore, as much electric power can be supplied to the monitoring chip if high-frequency electric power from the inspection device is increased, there is practically no problem. Further, as more electric power can be stored if the capacity of the capacitor C1 built in the monitoring chip is increased and an interval of data transmission is extended, that is, charging time is extended, normal operation is enabled even if the power consumption of the transmitter circuit increases. That is, in the second radio interface according to this system that uses not the UWB telecommunication system but a narrow band telecommunication system, data can be also practically transmitted from the inside of concrete without a problem.

Figure 12:
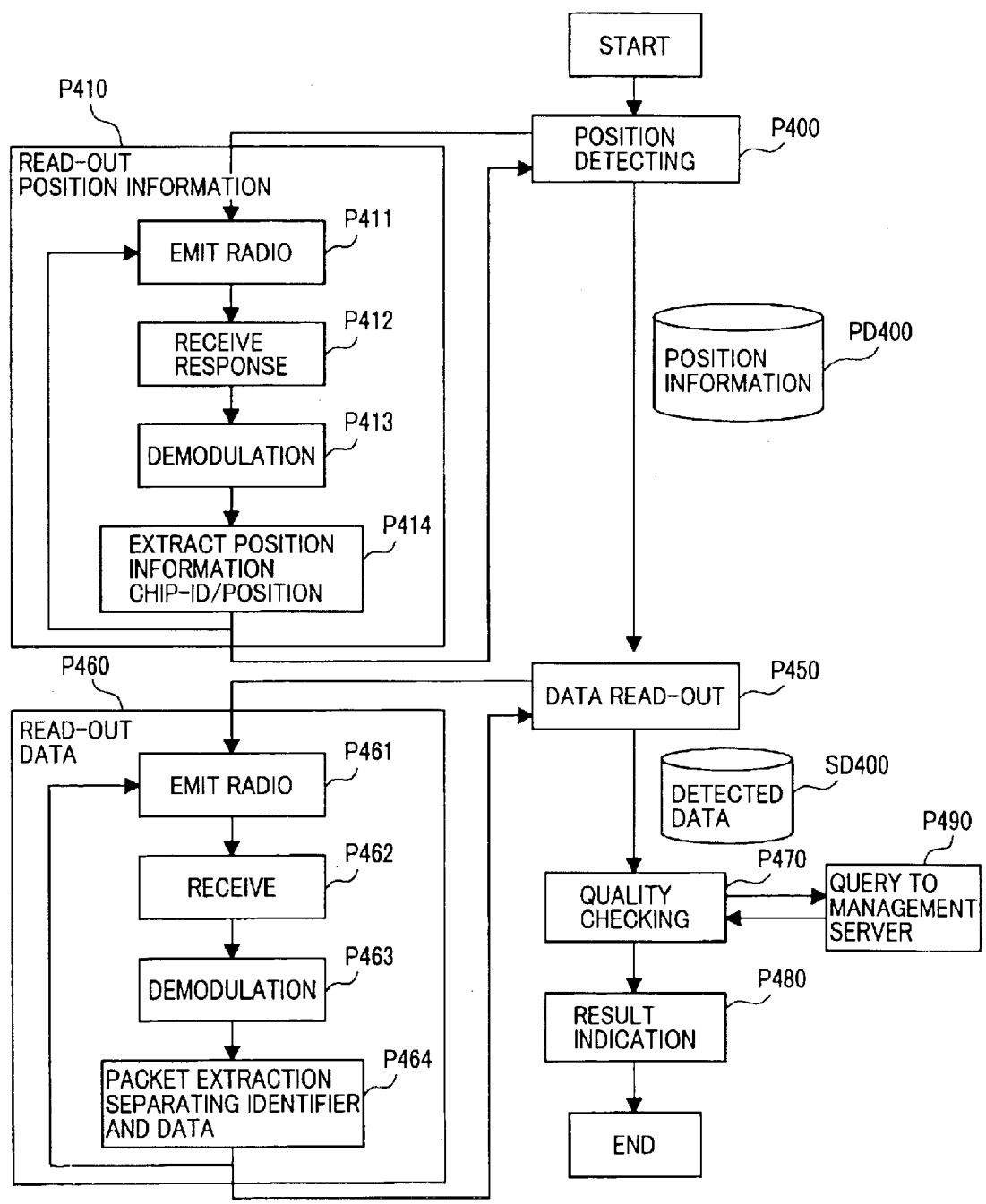
FIG. 12 shows the outline of the operation of a quality inspection device used in the quality monitoring system for building structure and the monitoring method according to the invention shown in FIG. 1.
Figure 13:
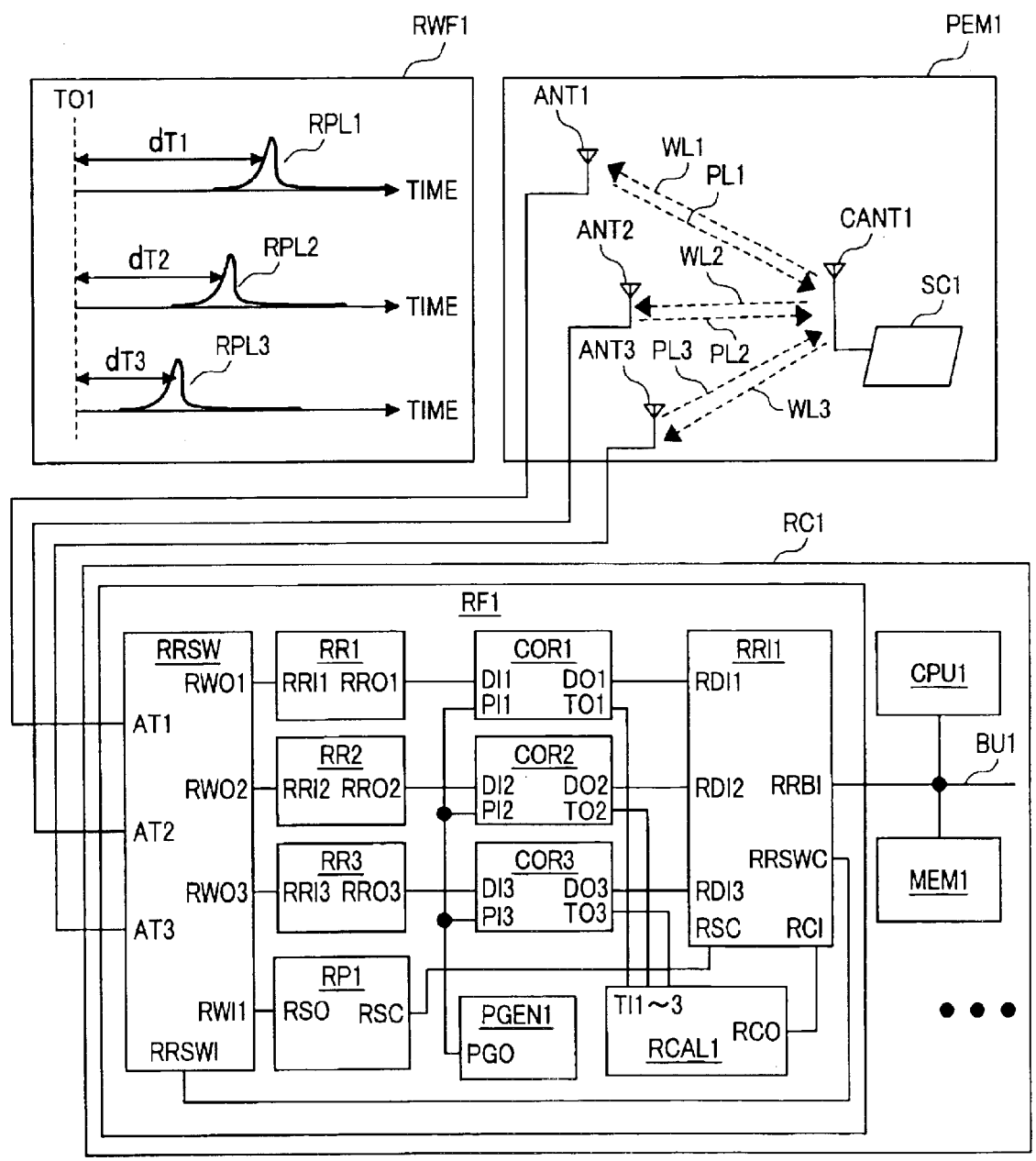
FIG. 13 shows the outline of data structure used in internal processing in the quality inspection device shown in FIG. 12.

The configuration and the operation of the monitoring chip according to the invention are described above, however, the operation of the inspection device RC1 that receives data from the monitoring chip and determines the quality of concrete will be described below. FIG. 12 is a flowchart showing the operation of a quality determination program (QPR1) installed in the inspection device RC1 according to the invention. Prior to quality checking, it is checked in a position detection routine (P400) and position information reading routines (P410 to P414) respectively specific to this inspection device where in concrete the monitoring chip is buried. It is made clear by reading data from the monitoring chip after the detection of the position of the monitoring chip as described above which part of building structure is made of concrete in what state. FIG. 13 shows an operational principle for detecting the position and the details of the configuration of a radio interface RF1 of the inspection device RC1. Referring to FIGS. 12 and 13, they will be described below. First, as shown in FIG. 13, high-frequency signals (PL1 to PL3) including only a carrier wave generated in a transmit amplifier that also functions as an oscillator PR1 in the radio interface RF1 are radiated toward the monitoring chip SC1 from antennas ANT1 to ANT3 installed mutually apart of the inspection device RC1 (the P411 routine). The monitoring chip SC1 is activated by the radiated high-frequency electric power as described above and transmits a signal including its own chip ID number (identifier) as data by radio. A radio wave transmitted from the monitoring chip is received via wireless connection (WL1 to WL3) (the P412 routine). The received signals (RPL1 to RPL3) are amplified up to a predetermined signal level in receive amplifiers (RR1 to RR3) via an antenna switching circuit RRSW in the radio interface RF1 of the inspection device RC1. Finally, the transmitted data is demodulated in correlators (COR1 to COR3) (the P413 routine). The correlators correlate a pulse train supplied from a pulse generator (PGEN1) and a received pulse train.

Figures 14A, 14B, 15:
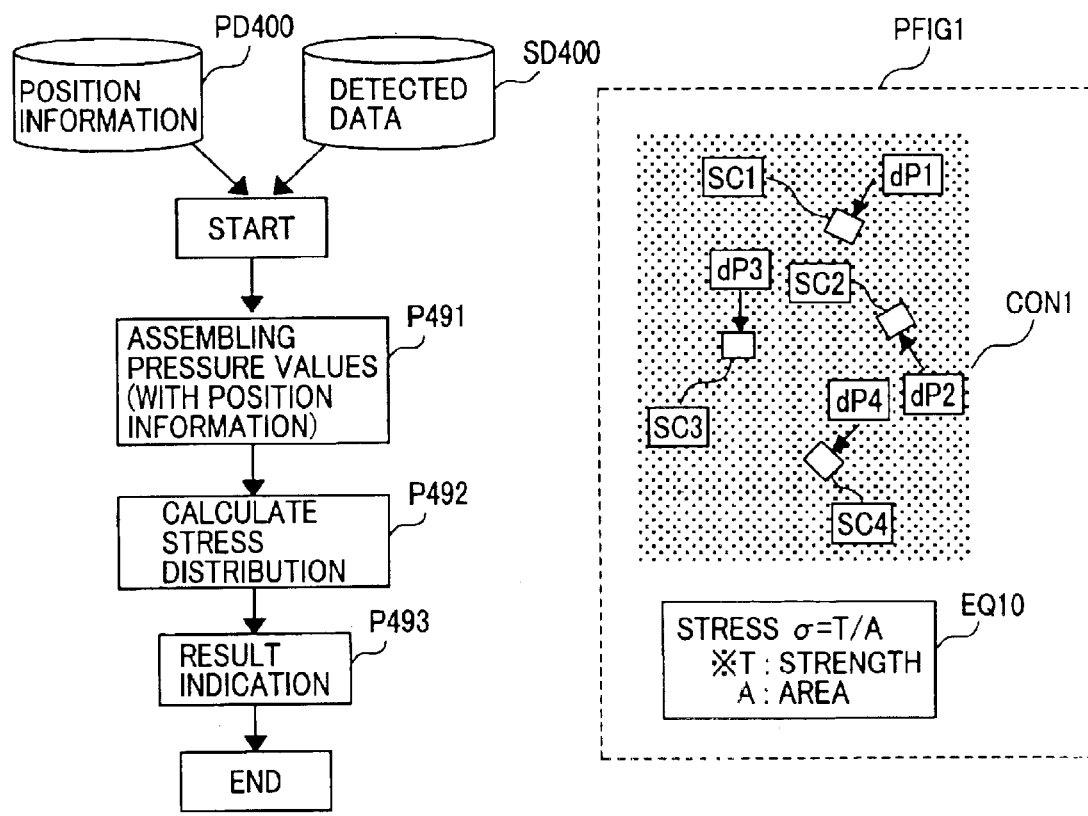
FIG. 15 explains a method of calculating stress distribution inside concrete and the principle by the monitoring system according to the invention.

Concretely, the correlators are circuits for detecting that the pulse train is in a position delayed by 100 psec for example and regenerating data. This correlator is generally composed of plural A/D converters. At the same time as data demodulation, the correlators also detect the respective arrival time (dT1 to dT3) shown in RWF1 in FIG. 13 of the received waves. The correlators calculate the position of the monitoring chip using a principle of so-called trilateration based upon difference between these arrival time (dT1 to dT3) and the information of locations of the antennas (ANT1 to ANT3)(the P414 routine) An arithmetic circuit for calculating a position (RCAL1) mounted in the radio interface RF1 as shown in FIG. 13 can calculate the position, however, calculated arrival time difference (dT1 to dT3) data is input to a processor (CPU1) in the inspection device RC1 and CPU1 can also calculate the position as software. As the receive amplifier, the correlators, the arithmetic circuit for calculating a position and the pulse generator are not specific to the invention, the detailed description is omitted. In case plural monitoring chips transmit data, the analysis of positional information is repeated by the number of demodulated identifiers of the monitoring chips. A file (PD400) in which the identifiers and the positional information of monitoring chips to be inspected by this inspection device RC1 are described is created. FIG. 14A shows an example of the data structure of this positional information file PD400. It is supposed in the description of the inspection device that radio communication is made in the UWB telecommunication system, however, if the correlator is substituted for a normal demodulator, an inspection device can be also configured by the similar configuration according to a telecommunication system such as QPSK and QAM.

The case that the position is detected using the three antennas (ANT1 to ANT3) is described above. However, as in the UWB telecommunication system, a signal is transmitted in the form of a pulse without a carrier wave, distance with the monitoring chip can be measured by only one antenna. That is, the position of the monitoring chip can be also detected by applying directivity to the antenna of the inspection device RC1, further enabling changing the direction of the antenna itself and sweeping, changing the direction of the antenna. The inspection device can be miniaturized by the above-mentioned configuration.

As described above, in the positional information reading routine P410, the identifier and the positional information of the monitoring chip that transmits data are acquired. Next, in the data reading routine, a data receiving routine P460 is activated and the reading of data from the monitoring chip is started. In the data receiving routine P460, as in the positional information reading routine P410, first in an RF radiating routine P461, electric power for data transmission is supplied to the monitoring chip. Next, in a receiving routine P462 and a demodulating routine P463, data from the monitoring chip activated by radiated high-frequency electric power is received and is demodulated according to the above-mentioned procedure. The identifier of the monitoring chip and the body of data are separated based upon the demodulated data (the P464 routine) and the result is written to a detection data file SD400. FIG. 14B shows an example of the data structure of the detection data file SD400. The above-mentioned processing is applied to all monitoring chips which have identifiers written to the positional information file PD400 created in the position detection routine and with which the inspection device can communicate and the detection data file SD400 is completed.

Next, in a quality determination routine P470, the quality of concrete is determined based upon the completed detection data file SD400. In this quality determination routine, it is judged based upon electric resistance values for example monitored by each monitoring chip and collected in the detection data file SD400 whether the quantity of moisture and chloride ions when concrete paste is prepared is adequate or not. In a P490 routine, a database DB10 in the management server SV10 installed on a wide area network WAN1 via the network interface NI1 built in the inspection device RC1 is accessed, the more detailed information of correlation between an electric resistance value and the quality of concrete for example is inquired and the precision of quality determination can be also enhanced. As described above, the determined result is displayed in a result display routine P480 and inspection is finished.

In the quality determination routine P470, in addition to the above-mentioned, for example, stress distribution in concrete is analyzed and can be also displayed. FIG. 15 shows an example of the configuration of a stress distribution analysis routine according to the invention which can be used for the object. As shown in PFIG1 in FIG. 15, in the monitoring system according to the invention, stress is acquired based upon local pressure inside concrete according to a stress defining expression EQ10. For example, according to an example shown in PFIG1, pressure dP1 to dP4 which the monitoring chips SC1 to SC4 receive is totalized referring to the detection data file SD400 (a P491 routine). At this time, stress distribution is calculated by adding the azimuth of each monitoring chip stored in the positional information file PD400 to the pressure information dP1 to dP4 (a P492 routine). Finally, the result is displayed or is transmitted to the management server and the processing is finished. As already described, the azimuth of each monitoring chip is calculated based upon a direction of gravity calculated based upon a D.C. component of an acceleration signal detected by the built-in acceleration sensor AS1 and the directions acquired in the position detection routine of the antennas ANT1 to ANT3 of the inspection device RC1.

The outline of the quality monitoring method for building structure according to the invention is described above, however, the invention is characterized in that the precision of inspection is enhanced by synthetically determining the quality based upon information from plural monitoring chips. That is, multiple monitoring chips are mixed inside concrete when concrete paste is prepared beforehand so that plural monitoring chips exist in a part in which the quality is to be determined. In inspection, data which have been monitored by these plural monitoring chips are acquired and basically, the quality is judged according to a principle of majority decision for example, in case three monitoring chips exist at a point to be measured, two monitoring chips of them report that the quantity of moisture is abnormal and remaining one reports that the quantity of moisture is normal, it is determined according to majority decision that the quantity of moisture is abnormal. Conversely, in case more monitoring chips report that the quantity of moisture is normal, it is determined that the quantity of moisture is normal. As described above, in case a part of monitoring chips malfunction or in case data reception from the monitoring chip malfunctions because of noise, a risk that wrong quality determination is made can be avoided by adopting the principle of majority decision to determine the quality. As described above, the monitoring chip according to the invention is manufactured in a semiconductor process in which the more monitoring chips are manufactured, the lower the manufacturing cost is. Therefore, many monitoring chips can be installed in concrete at an extremely low price and the above-mentioned excellent characteristics with which the monitoring system and the monitoring method according to the invention are provided can be utilized at the maximum. In the meantime, in the monitoring system and the monitoring method introduced in the prior art, the sensor is very high-priced and only one sensor is basically arranged at one measurement point. Therefore, a risk that wrong determination is made is considered considerably high. Further, it is considered that in case the sensor fails, the whole system may malfunction.

As described above, as in the monitoring chip according to the invention, transmitted electric power is limited, inspection at a time in the inspection device RC1 is limited to a range of approximately a few m. Therefore, to check the quality of the whole building structure, a mobile device is provided to the inspection device RC1, is moved inside the building structure and the P400 to P450 routines are required to be executed for the whole building structure. As simultaneous processing is enabled if plural inspection devices are prepared, it is thought that limited transmitted electric power does not practically come into question, however, it is expected that in case the building structure is to be eternally monitored, the limited transmitted electric power comes into question. It is a monitoring system provided with a relay shown in FIG. 16 that is designed to solve the problem.

Figure 16A:
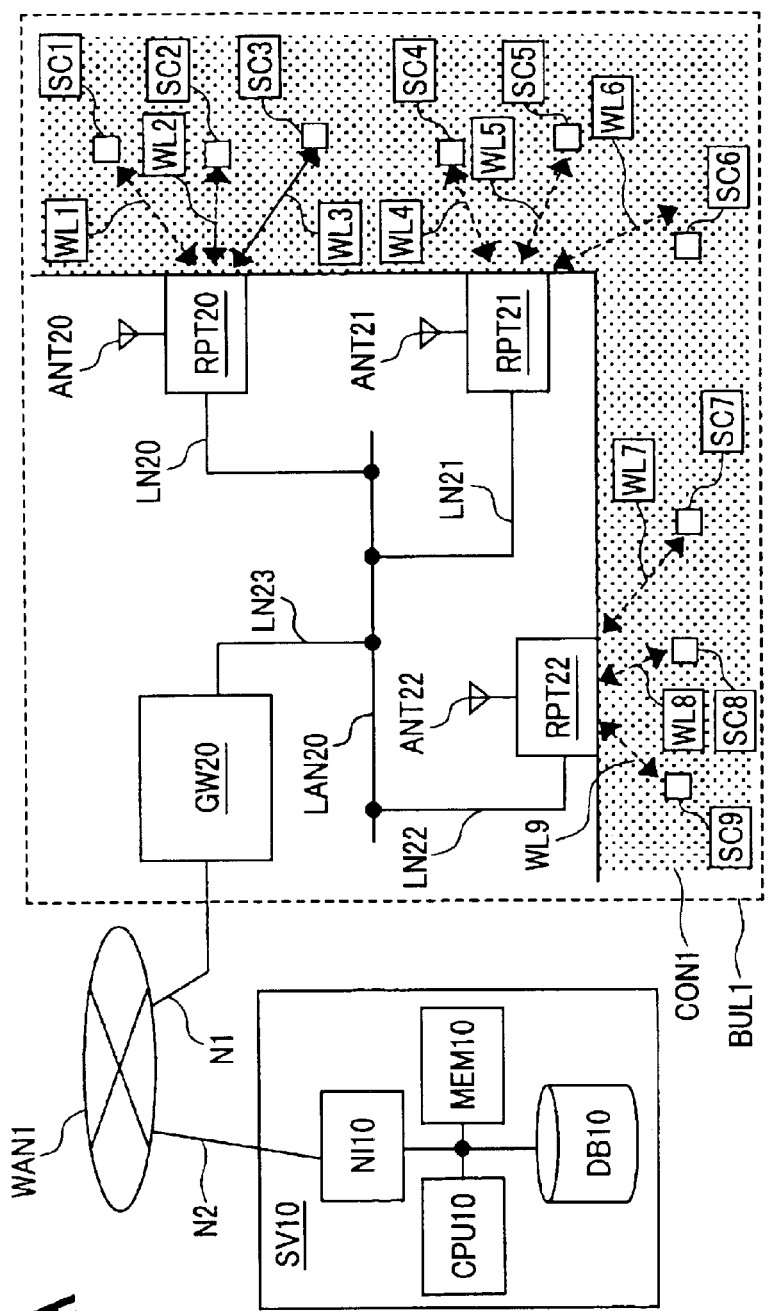
FIG. 16 show the concept of the relay of detection data by a relay described in a second embodiment and the configuration of a quality monitoring system for building structure utilizing the relay.
Figure 16B:
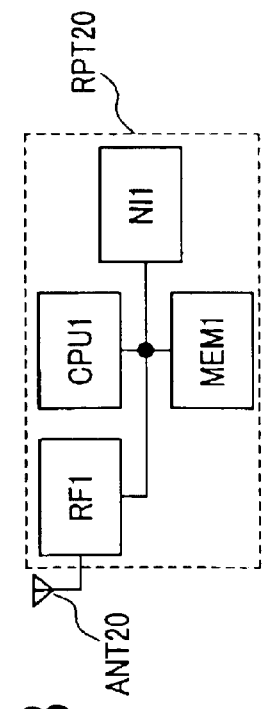

As shown in FIG. 16A, in this monitoring system, in place of the inspection device RC1, relays RPT20 to RPT22 are brought close to a wall/floor of concrete CON1 in building structure BUL1 and are arranged with them dispersed. These relays RPT20 to RPT22 are respectively typically composed of an antenna ANT20, a radio interface RF1, a processor CPU1, a memory MEM1 and a network interface NI1 as shown in FIG. 16B. The internal configuration of these circuits is basically similar to that of these circuits built in the inspection device RC1. These relays RPT20 to RPT22 are mutually connected to a gateway GW20 via local network interfaces LN20 to LN23 and LAN20. Besides, these relays can be connected to a wide area network WAN1 via the gateway GW20 and can be connected to a management server SV10 on WAN1.

The relays RPT20 to RPT22 communicate with near monitoring chips (SC1 to SC9) by radio (WL1 to WL3, WL4 to WL6, WL7 and WL8) according to a request from the management server SV10 or the gateway GW20 and report the result of monitoring to the management server via GW20. As already described, the request for data transmission is not required to be frequently made and at the shortest, the request has only to be made approximately once per hour. As described above, in the monitoring system provided with the relays shown in FIG. 16, building structure can be eternally monitored.

To supplement the above-mentioned, the invention is based upon a quality monitoring system for building structure composed of a semiconductor integrated circuit device in which sensors built in building structure for detecting physical quantity to be measured are mounted and an inspection device that receives a signal detected in the semiconductor integrated circuit device and determines the quality of the building structure based upon the received detect signal and is characterized in that proper ID number is stored in a memory mounted in the semiconductor integrated circuit device and the semiconductor integrated circuit device transmits a detect signal to which the proper ID number is added to an inspection device, further, the invention is based upon a quality monitoring system for building structure in which a detect signal is transmitted from the semiconductor integrated circuit device to the inspection device by radio and is particularly characterized in that radio transmission from the semiconductor integrated circuit device to the inspection is made using a pulse train in an ultra wide band (UWB) telecommunication system.

Besides, the invention is based upon the quality monitoring system for building structure and is particularly characterized in that for a radio frequency band used for transmitting a detect signal from the semiconductor integrated circuit device to the inspection device, a frequency band of 2 GHz or less is used.

Further, the invention is based upon a quality monitoring method for building structure provided with a first step for building a semiconductor integrated circuit device mounting sensors for detecting physical quality to be measured in building structure, a second step for operating the sensors in the semiconductor integrated circuit device and detecting the physical quantity of concrete in the building structure, a third step for storing a detect signal in a memory mounted in the semiconductor integrated circuit device, a fourth step for reading the detect signal stored in the memory mounted in the semiconductor integrated circuit device, a fifth step for transmitting the read detect signal to an inspection device provided outside the semiconductor integrated circuit device and a sixth step for determining the quality of the building structure based upon the detect signal transmitted to the inspection device and is particularly characterized in that in the fourth step, the detect signal is transmitted by radio from the semiconductor integrated circuit device to the inspection device.

Besides, the invention is based upon the quality monitoring method for building structure and is particularly characterized in that in the fifth-step, data is transmitted from the semiconductor integrated circuit device to the inspection device in the form of a radio signal the used frequency band of which is 2 GHz or less.

Besides, the invention is based upon the quality monitoring method for building structure and is particularly characterized in that a seventh step for detecting the position of the semiconductor integrated circuit device built in the building structure is provided after the sixth step and is particularly in that the inspection device provided with plural antennas receives a radio electric wave signal from the semiconductor integrated circuit device built in the building structure and detects the position of the semiconductor integrated circuit device based upon difference in arrival time between radio electric wave signals.

Further, the invention is based upon the quality monitoring system for building structure and the quality monitoring method for building structure and is characterized in that for the semiconductor integrated circuit device, a semiconductor integrated circuit device provided with a sensor that detects physical quantity to be measured, an A/D converter that amplifies a signal detected by the sensor and converts it to a digital signal, a microprocessor that processes the digital signal, a memory that stores information acquired by the sensor, a transmitter circuit that transmits the signal processed by the microprocessor to an external device and an electric power generator for supplying electric power to the sensor, the A/D converter, the microprocessor, the memory and the transmitter circuit is used.

Further, the invention is based upon a semiconductor integrated circuit device provided with provided with a sensor that detects physical quantity to be measured, an A/D converter that amplifies a signal detected by the sensor and converts it to a digital signal, a microprocessor that processes the digital signal, a memory that stores information acquired by the sensor, a transmitter circuit that transmits the signal processed by the microprocessor to an external device and an electric power generator for supplying electric power to the sensor, the A/D converter, the microprocessor, the memory, the transmitter circuit and is characterized in that the semiconductor integrated circuit device is provided with an electric power scavenging circuit that scavenges the increase by vibration of the electrostatic energy of a variable capacitor and converts it to electrical energy, an electric power controller and a capacitor, the electric power controller controls whether electric power generated by the electric power generator is supplied to the sensor, the A/D converter, the microprocessor, the memory and the transmitter circuit or not, the electric power generator is provided with a variable capacitor formed in a micro electro mechanical system (MEMS) process, the capacitor stores electric power generated by the electric power generator, the transmitter circuit transmits using a pulse train in an ultra wide band (UWB) telecommunication system, proper ID number is stored in the memory, at least a pressure sensor is provided as the sensor, and the sensor, the A/D converter, the microprocessor, the memory, the transmitter/receiver circuit and the electric power controller are formed on one semiconductor substrate.

Besides, the invention is based upon the quality monitoring system for building structure and the quality monitoring method for building structure and is particularly characterized in that plural semiconductor integrated circuits are buried in building structure and the quality of the building structure is checked based upon plural detect signals transmitted by radio from the semiconductor integrated circuit.

As described above, the system for monitoring the quality of concrete since concrete paste is prepared, which was heretofore impossible can be realized by using the monitoring chip according to the invention. Concretely, if the monitoring chip according to the invention is used, information of whether the management of temperature when concrete is cured is adequate or not or whether the quantity of moisture and chloride ions in concrete paste is adequate or not or whether a state of stress inside concrete is in question or not can be monitored by the temperature sensor, the electric resistance sensor and the pressure sensor respectively built in the monitoring chip. Further, if the monitoring chip according to the invention is used, building structure in which the quality monitoring system is built can be realized by mixing the monitoring chip with other concrete materials when concrete paste is prepared at an additional cost which can be substantially ignored according to a normal building structure constructing method. Besides, as the monitoring chip can be manufactured in a semiconductor integrated circuit manufacturing process, the quality monitoring system for building structure can be provided at a very low price. Further, according to the monitoring chip according to the invention, the quality of concrete can be eternally monitored owing to the built-in electric power generator and the ultralow power consumption operating system.

Second Embodiment

Figure 17:
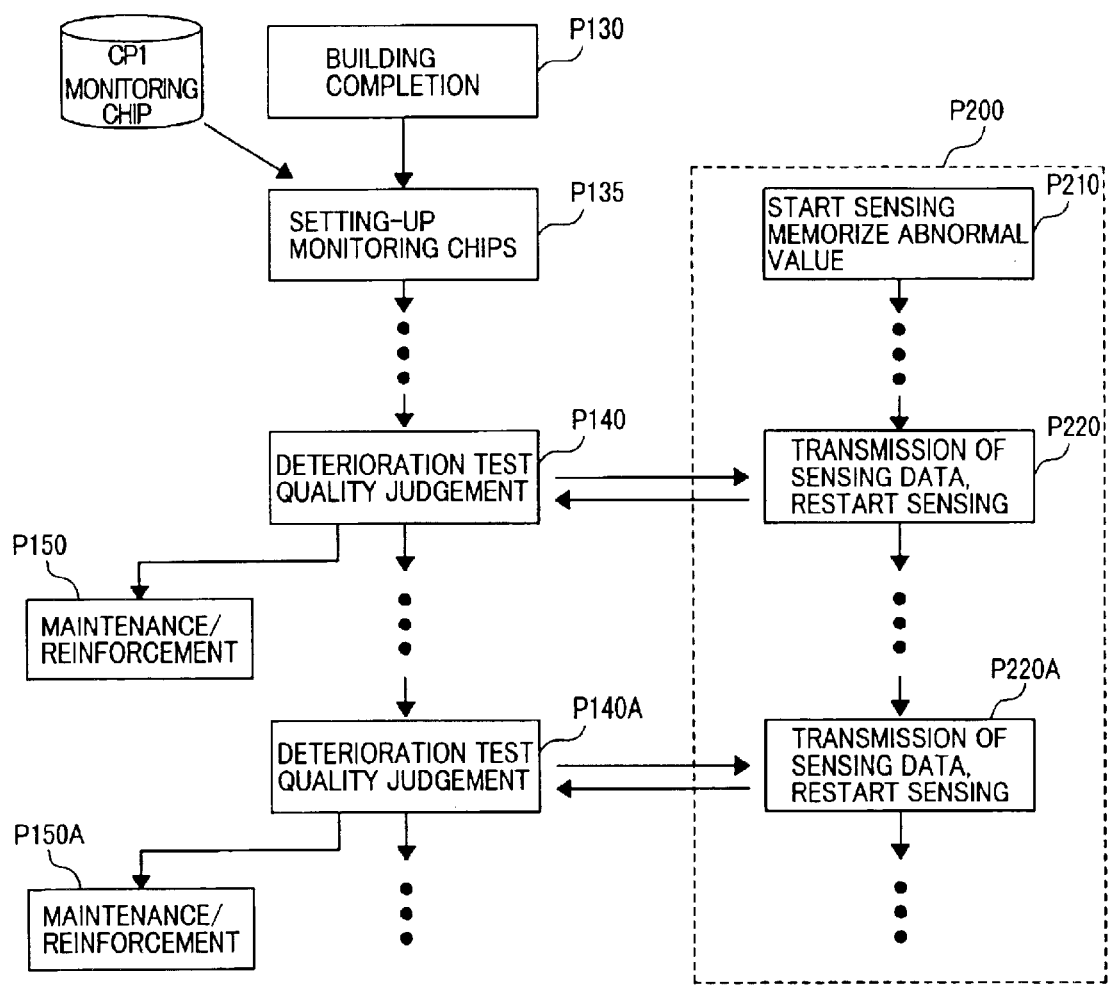
FIG. 17 shows a second quality monitoring method for building structure according to the invention.
Figure 18:
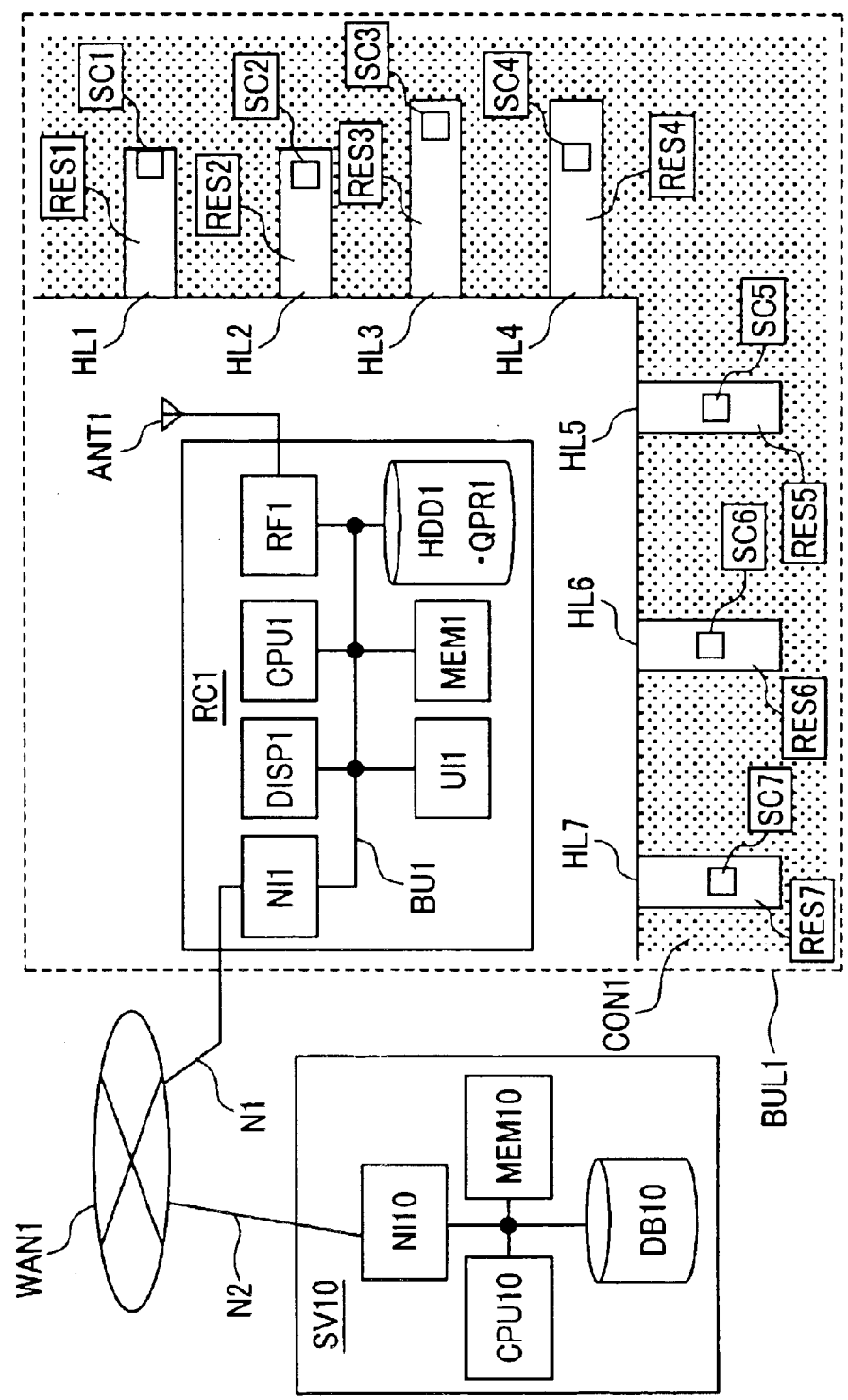
FIG. 18 shows the configuration of the monitoring system corresponding to the second quality monitoring method for building structure according to the invention shown in FIG. 17.

In the first embodiment, the method of configuring the monitoring system according to the method of mixing the monitoring chip according to the invention when concrete paste is prepared according to the procedure shown in FIG. 4 is described. In the meantime, in this embodiment, an example in which the quality monitoring system for building structure, the quality monitoring method for building structure and the monitoring chip according to the invention are applied to the existing building structure will be described (FIG. 17). In such a case, first, in a monitoring chip installation routine P135, this monitoring chip is installed in building structure. Various installation methods are conceivable, however, typically, as shown in FIG. 18, installing holes (HL1 to HL7) are made in a wall or a floor of concrete CON1 and monitoring chips (SC1 to SC7) are installed. Further, the installing holes HL1 to HL7 are sealed with resin (RES1 to RES7) such as epoxy resin. To prevent this monitoring chip from detecting moisture and others from the outside by mistake, it is desirable that the installing holes are sealed with resin as described above. As in the first embodiment, the monitoring chip generates electric power and starts sensing operation (P210). After adequate time elapses, the inspection device RC1 shown in FIG. 1 radiates a high frequency, activates the monitoring chip, the monitoring chip reads data stored in a memory and determines the quality (P220, P140). As a result of the quality determination, maintenance/reinforcement is made if necessary.

When the monitoring chip is installed after the building structure is completed as described above, the quality when concrete paste is prepared which has the greatest effect upon the quality of concrete cannot be monitored. However, actually, a great many concrete buildings already exist and it is not realistic to destroy all buildings and reconstruct by the method shown in FIG. 4. Further, in case the deterioration of concrete proceeds, a crack is caused, water permeates from the crack or the corrosion of concrete proceeds and electric resistance changes even if the monitoring chip is installed by the method shown in FIG. 18, the above-mentioned problems can be sufficiently detected by the monitoring system and the monitoring method equivalent to this embodiment. As described above, even if the monitoring chip is installed since building structure is completed, the monitoring system, the monitoring method and the monitoring chip according to the invention can be sufficiently utilized.

Third Embodiment

In the first embodiment, the example in which the monitoring system is configured by the monitoring chip which can be eternally operated by the built-in electric power generator as shown in FIG. 3 is described. In the meantime, as already described many times, it is the quality of concrete when concrete paste is prepared that has the greatest effect upon the quality of concrete. That is, depending upon an object, a case that only P100 to P120 and P210 to P220 shown in FIG. 4 have only to be monitored also exists.

Figure 19A:
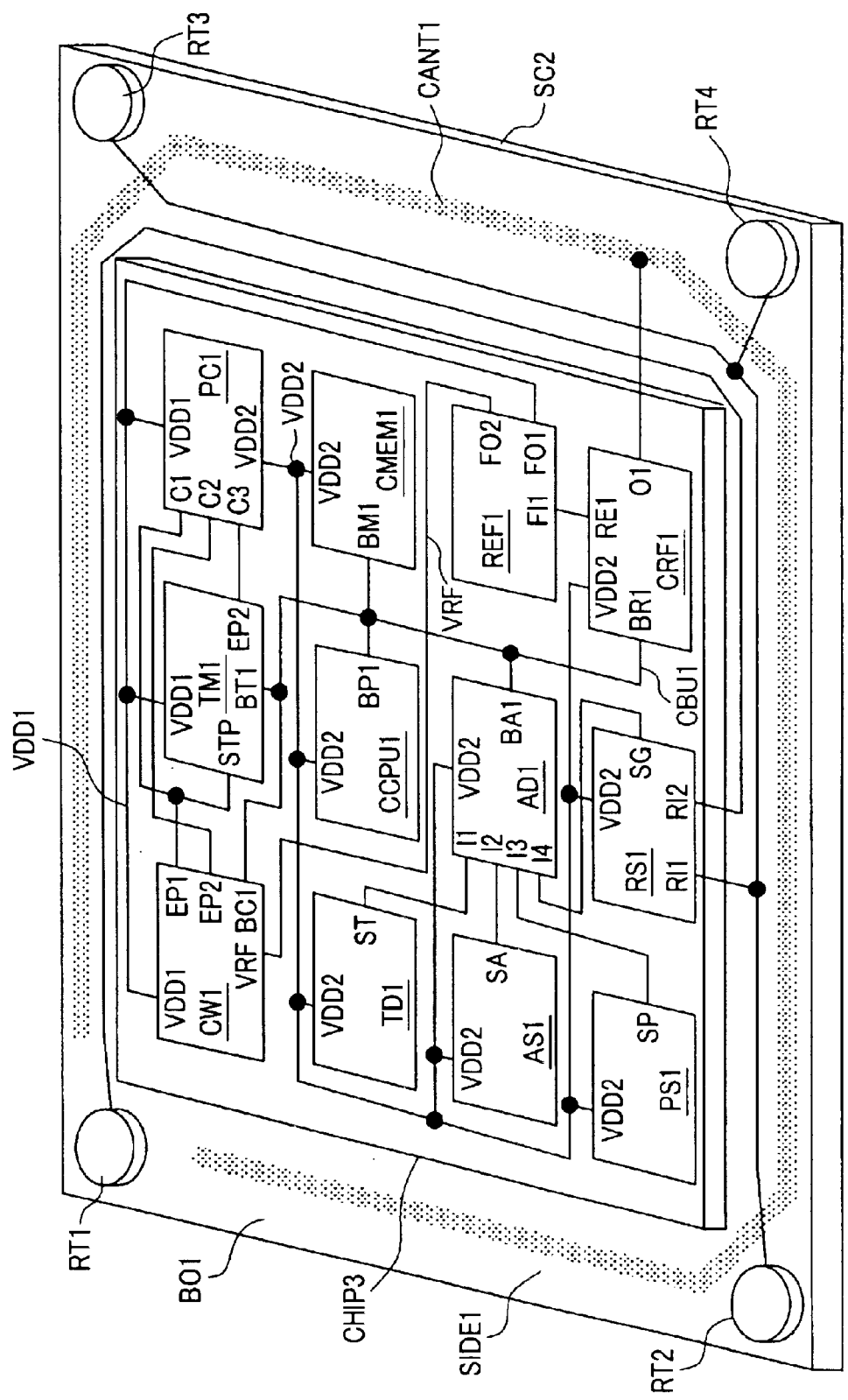
FIG. 19 show an example of the second configuration of a monitoring chip according to the invention described in a third embodiment.
Figure 19B:
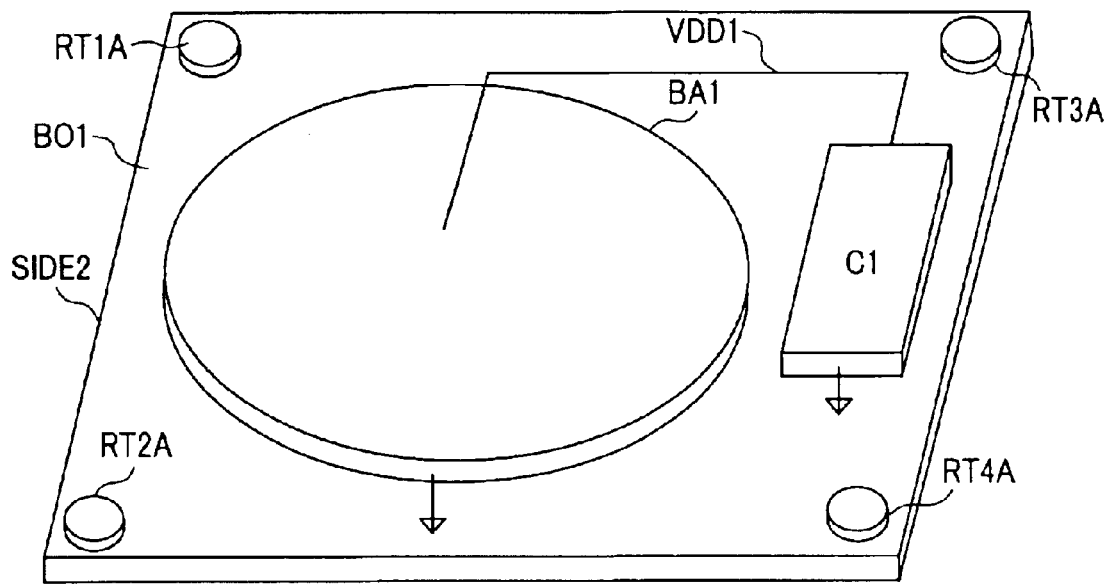
Figure 19C:
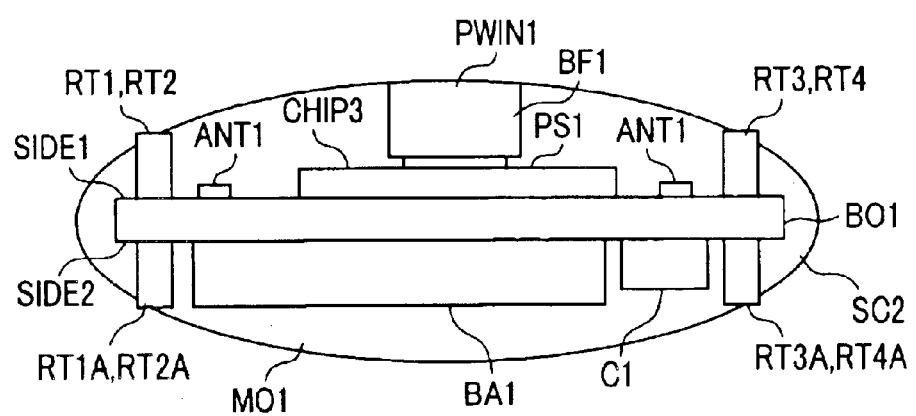

FIGS. 19A to 19C show an example of the configuration of a second monitoring chip according to the invention suitable for the object. As shown in FIG. 19, in this monitoring chip, differently from the example shown in FIG. 3, a button battery BA1 is mounted in place of the semiconductor integrated circuit for generating electric power. More detailedly, a first semiconductor integrated circuit CHIP1 is mounted on the upper surface (SIDE1) of a substrate BO1, the button battery BA1 is mounted on the reverse surface (SIDE2) of the substrate BO1 and the package of them is molded by epoxy resin with the similar structure to that shown in FIG. 2.

For the button battery BA1, generally sold various ones are available, however, even a button battery the diameter of which is 1 cm or less has the capacity of approximately 100 mAH (milliampere hour). That is, even if 100 $\mu$W/sec is required per one sensing operation and 1 mW/10 sec is required per one data transmission operation, sensing: to 1E−4 mA·sec=5.5E−8 mAH data transmission: to 1E−2 mA·sec=5.5E−6 mAH and the power consumption per once is an ignorable value, compared with the capacity.

When the battery is actually used, the life of the battery itself is required to be considered. Therefore, even if the power consumption per once is little, a usable period for the life of the battery is limited. However, generally, a battery has a few years' life. Therefore, even if a period since this monitoring chip is manufactured until it is actually buried and used is considered, it can be sufficiently realized that the monitoring chip is operated only for P100 to P120 and P210 to P220 shown in FIG. 4 and the quality when concrete paste is prepared is monitored. As described above, in case the second monitoring chip according to the invention shown in FIG. 19 is used, the quality monitoring system for building structure provided with an excellent quality checking function can be also configured.

Further, though particularly not shown, the similar configuration to the configuration in this embodiment shown in FIG. 19 that a button battery is replaced with a chargeable secondary battery or an electric double-layer capacitor that can realize the capacitance of a few farad, high-frequency electric power is supplied at an adequate time interval from an external device, the secondary battery or the electric double-layer capacitor is charged via an antenna CANT1 and a rectifier RF1 and a sensor is driven by the charged electric power is also possible. The secondary battery has only a life to the similar extent to that of the button battery, however, the life of the electric double-layer capacitor is by far longer. Therefore, if a battery is repeatedly charged at an adequate time interval, it can be used for monitoring the quality of building structure for a few years or more. In case the battery is used for the object, the monitoring system provided with relays shown in FIG. 16 is suitable.

Fourth Embodiment

In this embodiment, referring to FIG. 20, an example in which the monitoring system, the monitoring method and the monitoring chip according to the invention are applied to building structure except those in the above-mentioned embodiments will be described.

Figure 20A:
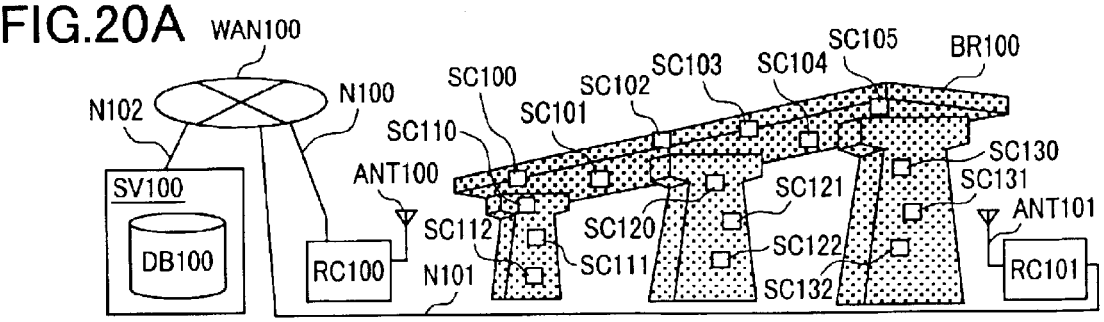
FIG. 20 show examples of other application described in a fourth embodiment of the quality monitoring system for building structure, the monitoring method and the monitoring chip according to the invention.

FIG. 20A shows an example in which the invention is applied to the quality monitoring of a bridge pier (BR100). As shown in FIG. 20A, the bridge pier BR100 is constructed according to the procedure shown in FIG. 4. That is, monitoring chips (SC100 to SC132) according to the invention are buried in concrete for forming the bridge pier, as described in the first embodiment, the quality of concrete since concrete paste is prepared is monitored and abnormal values are stored in a memory. When the curing of concrete is finished, data in the monitoring chip is read by a management server SV100 via inspection devices RC100 and RC101, networks N100 to N102 and WAN 100 and the quality of the bridge pier BR100 is determined. RC100 and RC101 denote the inspection device, however, the inspection device is configured by relays and a gateway as shown in FIG. 16 and eternal monitoring may be also enabled. It is made quite obvious by using the monitoring system according to the invention for the bridge pier as described above whether inadequate concrete is used or not. Therefore, inadequate concrete can be prevented from being used and a high quality of concrete bridge pier is acquired. In FIG. 20A, only the monitoring chips SC100 to SC133 are shown for explanation, however, actual use is not limited to this configuration (also similar in the following drawings).

Figure 20B:
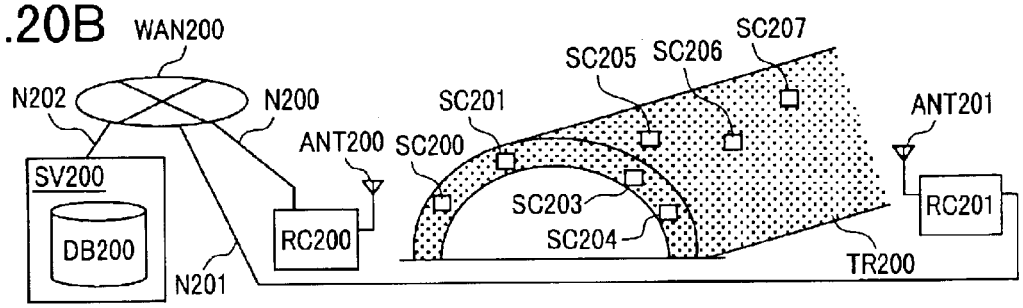

Next, FIG. 20B shows an example in which the invention is applied to monitoring the quality of a tunnel (TR200). The tunnel TR200 is similarly constructed according to the procedure shown in FIG. 4 and the monitoring chips (SC200 to SC207) according to the invention are buried in concrete for forming the tunnel. These monitoring chips monitor the quality of concrete since concrete paste is prepared and store abnormal values in the memory. When the curing of concrete is finished, data in the monitoring chip is read by a management server SV200 via inspection devices SC200 and SC201, networks N200 to N202 and WAN 200 and the quality of the tunnel TR200 is determined. RC200 and RC201 denote the inspection device, however, the inspection device is configured by relays and a gateway as shown in FIG. 16 and eternal monitoring may be also enabled.

Figure 20C:
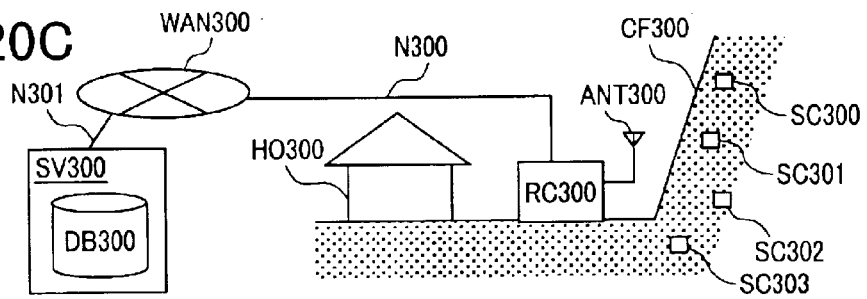

Next, FIG. 20C shows an example in which the monitoring chip according to the invention is installed on a precipice (CF300) and is used for detecting disaster. The monitoring chips (SC300 to SC303) according to the invention are similarly buried in a part made of concrete of the precipice CF300 according to the procedure shown in FIG. 4. In the case of a precipice not made of concrete, the monitoring chips are installed by the similar method to that shown in FIG. 18, that is, making holes in the precipice and burying the monitoring chips. In the monitoring chips SC300 to SC303 installed as described above, the quantity of moisture in earth and sand in the precipice or in a part made of concrete is monitored by an electric resistance sensor. Vibration in the precipice can be monitored by an acceleration sensor built in the monitoring chip. The result of the monitoring is periodically read by an inspection device RC300 (or relays and a gateway) and is transmitted to a management server SV300 via networks N300 and N301 and WAN300. A system that an alarm is automatically sounded before landslide is caused when earth and sand forming the precipice include a large quantity of moisture in which landslide may be caused or when vibration caused by a small-scale fall of earth immediately before large-scale landslide is caused is detected can be configured by such a monitoring system. For such an alarm system, it is demanded how to reduce malfunction. As described in the first embodiment, in the monitoring method according to the invention, wrong determination can be possibly avoided by dispersing plural monitoring chips at a measurement point and deciding information collected by the monitoring chips by majority. Therefore, the configuration of the excellent alarm system for landslide hardly sounded by mistake is enabled by the monitoring system according to the invention.

Figure 20D:
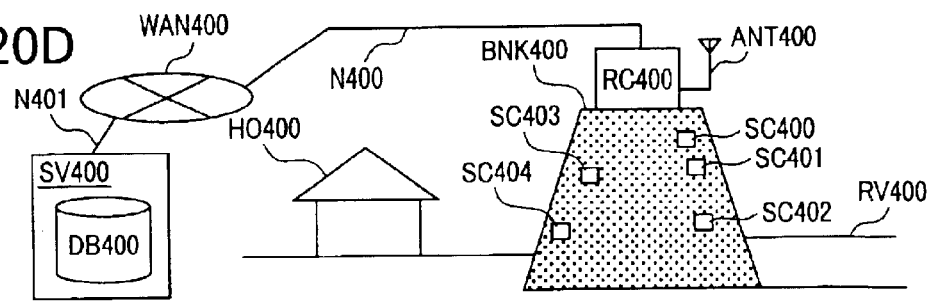

Further, FIG. 20D shows an example in which the alarm system is applied to a monitoring system for an embankment of a river (BNK400). The monitoring chips (SC400 to SC404) according to the invention are similarly buried in a part made of concrete of the embankment BNK400 according to the procedure shown in FIG. 4. In a part not made of concrete, the monitoring chips are installed by similarly making holes and burying the monitoring chips. In the monitoring chips SC400 to SC404 installed as described above, the quantity of moisture in earth and sand in the precipice or in a part made of concrete is monitored by an electric resistance sensor. Vibration in the precipice is monitored by an acceleration sensor built in the monitoring chip. The result of the monitoring is periodically read by an inspection device RC400 (or relays and a gateway), is transmitted and monitored to/by a management server SV400 via networks N400 and N401 and WAN400. A system that an alarm is automatically sounded when the river RV400 swells and water floods inside the embankment or when vibration caused by the small-scale collapse of the embankment immediately before large-scale collapse is caused is detected can be configured by such a monitoring system. As shown in FIG. 20C, wrong determination can be possibly avoided by dispersing plural monitoring chips at a measurement point and deciding information collected by these chips by majority. As described above, according to the invention, the excellent embankment collapse alarm system hardly sounded by mistake can be configured.

Figure 20E:
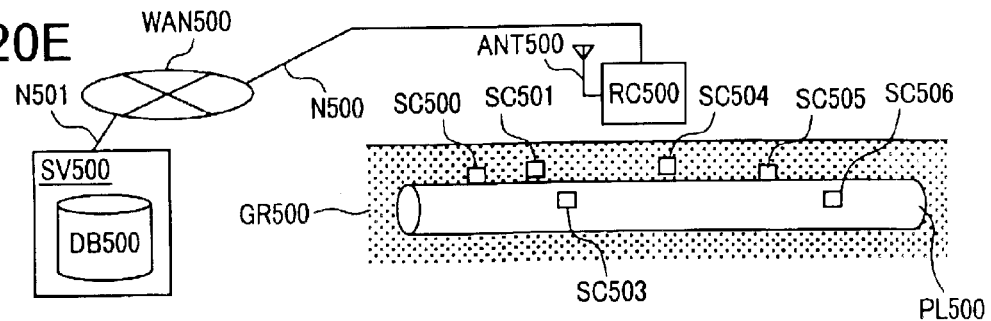

Further, FIG. 20E shows one embodiment in which the sensor chip according to the invention is used for an underground installation-type infrastructure PL500 such as a gas pipeline, an aqueduct and a power line. As shown in FIG. 20E, the monitoring chips (SC500 to SC506) according to the invention are installed in the ground near to the underground installation-type infrastructure by burying the monitoring chips after they are bonded to the underground installation-type infrastructure PL500 by an adhesive or by simultaneously burying the monitoring chips when the infrastructure is buried in the ground GR500. This monitoring chip generates electric power in a built-in semiconductor integrated circuit for generating electric power when the monitoring chip detects the minute vibration of the ground or minute vibration caused by the underground infrastructure such as the flow of water in the aqueduct and drives a sensor. Concretely, in case the underground infrastructure PL500 is the aqueduct, it is monitored by measuring electric resistance in soil around the aqueduct by a built-in electric resistance sensor whether the aqueduct leaks or not. Besides, in the case of the gas pipeline, in case gas leaks, gas leakage can be detected by detecting the variation of pressure caused by the gas leakage by a built-in acceleration sensor. Further, in the case of the power line, it is detected by the electric resistance sensor whether current leaks or not. As in the above-mentioned embodiments, the result of monitoring stored in memories of the monitoring chips SC500 to SC506 is periodically read by an inspection device RC500 (or relays and a gateway), is transmitted to a management server SV500 via networks N500 and N501 and WAN500 and it is determined whether a location of water leakage/gas leakage/a leak exists or not. As in the above-mentioned embodiments, wrong determination can be possibly avoided by dispersing plural monitoring chips at a measurement point and deciding information monitored by the chips by majority. As described above, the excellent water leakage/gas leakage/leak alarm system hardly sounded by mistake can be configured by the monitoring system according to the invention. Further, the monitoring system according to the invention can be also used for determining whether buried structure exists underground or not.

According to the above-mentioned embodiments, monitoring the information of whether the management of temperature when concrete is cured is adequate or not, whether the quantity of moisture and the quantity of included chloride ions of concrete paste are adequate or not or whether a state of stress inside concrete is in question or not is enabled by the temperature sensor, the electric resistance sensor and the pressure sensor respectively built in the monitoring chip.

The invention made by the inventors has been concretely described based upon the embodiments, however, the invention is not limited to the embodiments and it need scarcely be said that the invention can be variously changed in a range which does not deviate from the object. For example, the quality monitoring system for building structure/the quality monitoring method for building structure/the monitoring chip according to the invention are not limited to monitoring the quality of building structure but can be also applied to the system for detecting disaster such as the collapse of a precipice and the collapse of an embankment and the water leakage/gas leakage/leak alarm system. As described above, the invention can be applied to various fields and can be used for the similar monitoring system and the similar alarm system except the above-mentioned embodiments.

According to the invention, the system for monitoring the quality of concrete of building structure since concrete paste is prepared, which was heretofore impossible can be realized. Further, as the monitoring chip can be mixed with other concrete materials when concrete paste is prepared, building structure in which the monitoring chips are built can be realized at a low cost using a normal building structure constructing method. Besides, as the monitoring chip according to the invention can be manufactured in a semiconductor integrated circuit manufacturing process, the quality monitoring system for building structure can be provided at a very low price. Further, as the monitoring chip according to the invention is provided with the electric power generator and adopts the ultralow power consumption operating method, the quality of concrete of building structure can be eternally monitored.

What is claimed is:

1. A quality monitoring system for building structure, comprising:

a semiconductor integrated circuit device which is built in the building structure including a sensor to detect a physical quantity related to the property of the building structure and a power circuit to apply power to the sensor; and an inspection device that receives a detect signal generated based upon the physical quantity detected by the semiconductor integrated circuit device and determines the quality of the building structure based upon the received detect signal, wherein the power circuit intermittently applies power to the sensor; and wherein the sensor detects the physical quantity when the power circuit applies power to the sensor.

2. A quality monitoring system for building structure according to claim 1, wherein:

the semiconductor integrated circuit device is provided with a memory;

the memory stores an ID number proper to the semiconductor integrated circuit device; and the semiconductor integrated circuit device transmits the ID number together with the detect signal to the inspection device.

3. A quality monitoring system for building structure according to claim 1, wherein:

the semiconductor integrated circuit device is provided with a memory;

the memory stores a detect signal corresponding to the detected physical quantity; and the semiconductor integrated circuit device reads the detect signal from the memory according to a request from the inspection device and transmits it to the inspection device.

4. A quality monitoring system for building structure according to claim 1, wherein:

the detect signal is transmitted from the semiconductor integrated circuit device to the inspection device by radio.

5. A quality monitoring system for building structure according to claim 1, wherein:

the building structure is mainly made of concrete;

the semiconductor integrated circuit device is built in the building structure in a state of paste before the concrete is set; and the semiconductor integrated circuit device detects the physical quantity of the concrete in the state of paste and transmits the detect signal to the inspection device.

6. The quality monitoring system for building structure according to claim 1,
wherein the power circuit comprises a capacitor to store power, and a switch coupled to the capacitor and the sensor.

7. The quality monitoring system for building structure according to claim 6,
wherein the power circuit further comprises an electric power generator to generate electric power, and
wherein the capacitor receives the electric power from the electric power generator.

8. The quality monitoring system for building structure according to claim 7, further comprising:
a step for generating electric power from an electric power generator; and
a step for supplying the capacitor with the electric power.

9. A quality monitoring method for building structure, comprising steps of:
a step for mounting a sensor in the building structure for generating a detect signal corresponding to a physical quantity related to a property of the building structure;
a step for intermittently applying power to the sensor from a power circuit mounted on the semiconductor integrated circuit;
a step for intermittently detecting the physical quantity related to the property of the building structure, when the power is applied to the sensor, to generate the detect signal,
a step for transmitting the detect signal to an inspection device provided outside the semiconductor integrated circuit device; and
a step for determining the quality of the building structure based upon the detect signal received by the inspection device.

10. A quality monitoring method for building structure according to claim 9, wherein:
the semiconductor integrated circuit device further mounts a memory; and
the quality monitoring method for building structure further comprises steps of;
a step for storing the detect signal generated by the sensor in the memory; and
a step for reading the detect signal stored in the memory.

11. A quality monitoring method for building structure according to claim 10, wherein:
the step for reading the detect signal is a step for reading the detect signal stored in the memory according to a request from the inspection device.

12. A quality monitoring method for building structure according to claim 10, wherein:
the step for transmitting the detect signal to an inspection device provided outside the semiconductor integrated circuit device is a step for transmitting an ID number proper to the semiconductor integrated circuit device and stored in the memory together with the detect signal; and
the step for determining the quality is a step for specifying a semiconductor integrated circuit device that transmits the detect signal based upon the ID number transmitted from the semiconductor integrated circuit device together with the detect signal and determining the quality of the building structure.

13. A quality monitoring method for building structure according to claim 12, wherein:
the step for specifying a semiconductor integrated circuit device that transmits the detect signal and determining the quality of the building structure is a step detecting the position of the semiconductor integrated circuit device in the building structure and determining the quality of the building structure.

14. A quality monitoring method for building structure according to claim 9, wherein:
the step for transmitting the detect signal to an inspection device provided outside the semiconductor integrated circuit device is a step for transmitting the detect signal from the semiconductor integrated circuit device to the inspection device by radio.

15. A quality monitoring method for building structure according to claim 9, wherein:
the building structure is mainly made of concrete;
the step for building the semiconductor integrated circuit device in the building structure is a step for building the semiconductor integrated circuit device in the building structure in a state of paste before the concrete is set;
the step for generating the detect signal is a step for operating the sensor in a state of paste before the concrete is set, detecting the physical quantity related to the property of the building structure and generating the detect signal corresponding to the physical quantity; and
the step for transmitting the detect signal to an inspection device provided outside the semiconductor integrated circuit device is a step for transmitting the detect signal to the inspection device after the concrete is set.

16. A quality monitoring method for building structure according to claim 9, wherein:
the sensor includes at least one of an electric resistance sensor, a temperature sensor, a pressure sensor and an acceleration sensor.

17. The quality monitoring system for building structure according to claim 9, further comprising:
a step for storing power to a capacitor of the power circuit; and
a step for turning on a switch between the capacitor and the sensor to apply the power stored in the capacitor to the sensor.

18. A semiconductor integrated circuit device, comprising:
a sensor that detects physical quantity measurable by a semiconductor and related to the property of building structure;
an A/D converter that amplifies a signal detected by the sensor and converts the signal to a digital signal;
a microprocessor that processes the digital signal;
a transmitter circuit that transmits a signal processed by the microprocessor to an external device;
an electric power generator configured so that it supplies electric power to at least one of the sensor, the A/D converter, the microprocessor and the transmitter circuit;
an electric power controller that controls whether electric power generated by the electric power generator is supplied to at least one of the sensor, the A/D converter, the microprocessor and the transmitter circuit or not; and
a capacitor configured so that electric power generated by the electric power generator is stored.

19. A semiconductor integrated circuit device according to claim 18, further comprising:

a memory for storing information acquired by the sensor.

20. A semiconductor integrated circuit device according to claim 19, wherein:

the memory stores an ID number proper to a semiconductor integrated circuit device mounting the memory.

21. A semiconductor integrated circuit device according to claim 18, wherein:

the sensor includes a pressure sensor.

22. A semiconductor integrated circuit device according to claim 18, wherein:

the transmitter circuit transmits using a pulse train in an ultra wide band (UWB) telecommunication system.

23. A semiconductor integrated circuit device according to claim 18, wherein:

the electric power generator comprises:

a variable capacitor formed in an MEMS process; and an electric power scavenging circuit that scavenges the increase of the electrostatic energy of the variable capacitor by the vibration at the building structure and converts it to electrical energy.

24. A semiconductor integrated circuit device according to claim 18, wherein:

the sensor, the A/D converter, the microprocessor, the transmitter circuit and the electric power controller are formed on one semiconductor substrate.

25. A semiconductor integrated circuit device according to claim 18, wherein:

the electric power generator is formed on a second semiconductor chip separate from a first semiconductor chip where the sensor, the A/D converter, the microprocessor, the transmitter circuit and the electric power controller are formed; and the first semiconductor chip and the second semiconductor chip are mounted on reverse surfaces of a common substrate.

26. Building structure the quality of which can be determined by a quality monitoring system for building structure, wherein:

the quality monitoring system for building structure comprises:

a semiconductor integrated circuit device which is built in the building structure and in which a sensor for detecting physical quantity related to the property of the building structure is mounted; and an inspection device that receives a detect signal generated based upon physical quantity detected in the semiconductor integrated circuit device and determines the quality of the building structure based upon the received detect signal; and the semiconductor integrated circuit device comprises:

a sensor for detecting physical quantity measurable by a semiconductor and related to the property of building structure;

an A/D converter that amplifies a signal detected by the sensor and converts it to a digital signal;

a microprocessor that processes the digital signal;

a transmitter circuit that transmits the signal processed by the microprocessor to an external device;

an electric power generator configured so that it supplies electric power to at least one of the sensor, the A/D converter, the microprocessor and the transmitter circuit;

an electric power controller configured so that it controls whether electric power generated by the electric power generator is supplied to at least one of the sensor, the A/D converter, the microprocessor and the transmitter circuit or not; and a capacitor configured so that it stores electric power generated by the electric power generator.

27. Building structure in which a semiconductor integrated circuit device is buried and the quality of which can be determined by a quality monitoring method for building structure, wherein:

the quality monitoring method for building structure comprises steps of:

a step for building a semiconductor integrated circuit device mounting a sensor for detecting physical quantity related to the property of the building structure and generating a detect signal corresponding to the physical quantity in the building structure;

a step for operating the sensor, detecting the physical quantity related to the property of the building structure and generating the detect signal corresponding to the physical quantity;

a step for transmitting the detect signal to an inspection device provided outside the semiconductor integrated circuit device; and a step for determining the quality of the building structure based upon the detect signal received by the inspection device; and the semiconductor integrated circuit device comprises:

a sensor for detecting physical quantity measurable by a semiconductor and related to the property of building structure;

an A/D converter that amplifies a signal detected by the sensor and converts it to a digital signal;

a microprocessor that processes the digital signal;

a transmitter circuit that transmits the signal processed by the microprocessor to an external device;

an electric power generator configured so that it supplies electric power to at least one of the sensor, the A/D converter, the microprocessor and the transmitter circuit;

an electric power controller configured so that it controls whether electric power generated by the electric power generator is supplied to at least one of the sensor, the A/D converter, the microprocessor and the transmitter circuit or not; and a capacitor configured so that it stores electric power generated by the electric power generator.

28. Building structure, wherein:

a semiconductor integrated circuit device provided with a sensor for detecting physical quantity related to the property of the building structure is buried; and the quality can be determined based upon a detect signal corresponding to the physical quantity detected by the semiconductor integrated circuit device by the inspection device.

29. Building structure according to claim 28, wherein:

the semiconductor integrated circuit device further comprises:

an A/D converter that amplifies a signal detected by the sensor and converts it to a digital signal;

a microprocessor that processes the digital signal;

a transmitter circuit that transmits the signal processed by the microprocessor to an external device;

an electric power generator configured so that it supplies electric power to at least one of the sensor, the A/D converter, the microprocessor and the transmitter circuit;

an electric power controller configured so that it controls whether electric power generated by the electric power generator is supplied to at least one of the sensor, the A/D converter, the microprocessor and the transmitter circuit or not; and a capacitor configured so that it stores electric power generated by the electric power generator.

* * * * *